(12) United States Patent
Liu et al.

(10) Patent No.: US 7,053,201 B2
(45) Date of Patent: May 30, 2006

(54) NUCLEIC ACID MOLECULES AND POLYPEPTIDES RELATED TO H-ADAM7

(75) Inventors: Hwan-Wun Liu, Taipei (TW); Guang-Huan Sun, Hsinchu (TW); Yu-Chi Lin, Hsindian (TW); Sun-Yran Chang, Taipei (TW)

(73) Assignee: National Defense Medical Center, Taipei (TW)

( * ) Notice: Subject to any disclaimer, the term of this patent is extended or adjusted under 35 U.S.C. 154(b) by 164 days.

(21) Appl. No.: 10/232,972

(22) Filed: Aug. 30, 2002

(65) Prior Publication Data
US 2004/0043387 A1  Mar. 4, 2004

(51) Int. Cl.
*C07H 21/04* (2006.01)
*C12N 9/50* (2006.01)

(52) U.S. Cl. .................. 536/23.5; 435/219; 435/252.3; 435/320.1; 536/23.1; 536/23.2; 530/350

(58) Field of Classification Search ............... 536/23.1, 536/23.2, 23.5; 435/219, 320.1, 252.3; 530/350
See application file for complete search history.

(56) References Cited

FOREIGN PATENT DOCUMENTS
WO    WO 01/71004    *  9/2001

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*
Perry et al., Biochem J. vol. 286, pp 671-675, 1992.*
Cooper TG. Interactions between epididymal secretions and spermatozoa. J Reprod Fertil Suppl 1998; 53:119-36.
Jones RC. Evolution of the vertebrate epididymis. J Reprod Fertil Suppl 1998; 53:163-181.
Cooper TG. In defense of a function for the human epididymis. Fertil Steril 1990; 54:965-975.
Turner TT. On the epididymis and its role in the development of the fertile ejaculate. J Androl 1995; 16:292-298.
Myles DG. Molecular mechanisms of sperm-egg membrane binding and fusion in mammals. Dev Biol 1993: 158:35-45.
Cornwall GA, Hann SR. Specialized gene expression in the epididymis. J Androl 1995; 16:379-383.
Primakoff P, Myles DG. The ADAM gene family: surface proteins with adhesion and protease activity. Trends Genet 2000; 16:83-7.
Hemandez LD, Hoffman LR, Wolfsberg TG, White JM. Virus-cell and cell-cell fusion. Annu Rev Cell Dev Biol 1996; 12:627-661.
Stone AL, Kroeger M, Sang QXA. Structure-Function analysis of the ADAM family of disintegrin-like and metalloproteinase-containing protein. J Protein Chem 1999; 18:447-465.
Schlondorff J, Blobel CP. Metalloprotease-disintegrins: modular proteins capable of promoting cell-cell interactions and triggering signals by protein-ectodomain shedding. J Cell Sci 1999; 112:3603-3617.
Blobel CP, Wolfsberg TG, Turck CW, Myles DG, Primakoff P, White JM. A potential fusion peptide and an integrin ligand domain in a protein active in sperm-egg fusion. Nature 1992; 365:428-252.
Bigler D, Chen M, Waters S, White JM. A model for sperm-egg binding and fusion based on ADAMs and integrins. Trends Cell Biol 1997; 7:220-225.
Wolfsberg TG, Primakoff P, Myles DG, White JM. ADAM, a novel family of membrane proteins containing A Disintegrin And Metalloprotease domain: multipotential functions in cell-cell and cell-matrix interactions. J Cell Biol 1995; 131:275-278.
Wolfsberg TG, Straight PD, Gerena RL, Huovila AP, Primakoff P, Myles DG, White JM. ADAM, a widely distributed and developmentally regulated gene family encoding membrane proteins with A Disintegrin And Metalloprotease Domain. Dev Biol 1995; 169:378-383.
Primakoff P, Hyatt H, Tredick-Kline J. Identification and purification of a sperm surface protein with a potential role in sperm-egg membrane fusion. J Cell Biol 1987; 104:141-149.
Perry AC, Jones R, Baker PJ, Hall L. A mammalian epididymal protein with remarkable sequence similarity to snake venom haemorrhagic peptides. Biochem J 1992; 286:671-675.
Cornwall GA, Hsia N. ADAM7, a member of the ADAM (a disintegrin and metalloprotease) gene family is specifically expressed in the mouse anterior pituitary and epididymis. Endocrinology 1997; 138:4262-4272.
Liu HW, Lin YC, Chao CF, Chang SY, Sun GH. GP-83 and GP-39, two glycoproteins secreted by human epididymis were conjugated to sperm during maturation. Mol Hum Reprod 2000; 6:422-428.
Sun G-H, Lin Y-C, Guo Y-W, Chang S-Y, Liu H-W. Purification of GP-83, a glycoprotein secreted by human epididymis and conjugated to mature spermatozoa. Mol Hum Reprod 2000; 6:429-434.

(Continued)

*Primary Examiner*—Richard Hutson
(74) *Attorney, Agent, or Firm*—Finnegan, Henderson, Farabow, Garrett & Dunner, L.L.P.

(57) ABSTRACT

Novel GP-83 protein (human epididymis-associated disintegrin and metalloprotease 7 protein) and nucleic acid molecules are disclosed. The invention provides purified GP-83 protein, fusion protein, antigenic peptides, and anti-GP-83 antibodies. The invention also provides isolated GP-83 nucleic acid molecule, recombinant vectors containing the GP-83 nucleic acid molecule, host cells containing the recombinant vector, and non-human transgenic animals in which the GP-83 nucleic acid molecule has been introduced or interrupted.

4 Claims, 5 Drawing Sheets

OTHER PUBLICATIONS

Talbot P, Chacon RS. Ultrastructural observation on binding and zona pellucida-free hamster oocytes. Fertil Steril 1982; 27:240-248.

Yanagimachi R. Mammalian fertilization. In The Physiology of Reproduction. 2nd ed. New York: Raven Press; 1994, Chapter 5, 189-317.

Sambrook J, Fritsch EF, Maniatis T (eds.), Molecular Cloning: A Laboratory Manual. 2nd Ed. New York: Cold Spring Harbor; 1989.

Huynh TV, Young RA, Davis RW. Constructing and screening cDNA libraries in Agt10 and Agt11. In: Glover DM (ed.) DNA Cloning: A practical Approach, vol. 1, Oxford: IRL Press; 1985:49-78.

Pearson WR, Lipman DJ. Improved tools for biological sequence comparison. Proc Nat'l Acad Sci USA 1988; 85:2444-8.

Wolfsberg TG, White JM. ADAMs in fertilization and developoment. Devel Biol 1996; 180:389-401.

Hite LA, Fox JM, Bjarnason JB. A new family of proteinases is defined by several snake venom metalloproteinases. Bio Chem 1992; 373:381-385.

Alexandropoulos K, Cheng G, Baltimore D. Proline-rich sequences that bind to Src homology 3 domains with individual specificities. Proc Nat'l Acad Sci USA 1995; 92:3110-3114.

Van Wart HE, Birkedal-Hansen H. The cysteine switch: A principle of regulation of metalloproteinase activity with potential applicability to the entire matrix metalloproteinase gene family. Proc Nat'l Acad Sci USA 1990; 87:5578-5582.

Grams F, Huber R, Kress LF, Moroder L, Bode W. Activation of snake venom metalloproteinases by a cysteine switch-like mechanism. FEBS Letter 1993; 335:76-80.

Hynes RO. Integrins: a family of cell surface receptors. Cell 1987; 48:549-554.

Krätzschmar J, Lum L, Blobel CP. Metargidin, a Membrane-anchored Metalloprotease-Disintegrin Protein with an RGD Integrin Binding Sequence. J Biol Chem 1996; 271:4593-4596.

Herren B, Raines EW, Ross R. Expression of a disintegrin-like protein in cultured human vascular cells and in vivo. FASEB J 1997; 11:173-180.

Gupta S, Li H, Sampson NS. Characterization of fertilinβ-disintegrin binding specificity in sperm-egg adhesion. Bioorg Med Chem 2000; 8:723-729.

Pawson T. Protein modules and signaling networks. Nature 1995; 373:573-580.

Katagiri K, Harada Y, Emi M, Nakamura Y. Human metalloprotease/disintegrin-like (MDC) gene: exon-intron organization and alternative splicing. Cytogenet Cell Genet 1995; 68:39-44.

Cho C, Primakoff P, White JM, Myles DG. Chromosomal assignment of four testis-expressed mouse genes from a new family of transmembrane proteins (ADAMs) involved in cell-cell adhesion and fusion. Genomics 1996; 34:413-417.

Lemaire L, Johnson KR, Bammer S, Petry P, Ruddle FH, Heinlein UAO. Chromosomal assignment of three novel mouse genes expressed in testicular cells. Genomics 1994; 21:409-414.

Perry AC, Jones R, Hall L. Analysis of transcripts encoding novel members of the mammalian metalloprotease-like, disintegrin-like, cysteine-rich (MDC) protein family and their expression in reproductive and non-reproductive monkey tissue. Biochem J 1995; 312:239-244.

\* cited by examiner

B

```
   1 GATCCCTGCAGTGGAAGTGAGGAGGAAGAAAGGTGAACTCCTTTTCTCAAGCACTTCTGCTCTCCTCTACCAGAATCACTCAGAATGCTTCCCGGGTGT   99
 100 ATATTCTTGATGATTTTACTCATTCCTCAGGTTAAAGAAAAGTTCATCCTTGGAGTAGAGGGTCAACAACTGGTTCGTCCTAAAAAGCTTCCTCTGATA  198
 199 CAGAAGCGAGATACTGGACACACCCATGATGATGACATACTGAAAACGTATGAAGAAGAATTGTTTGTATGAAATAAAACTAAATAGAAAAACCTTAGTC  297
 298 CTTCATCTTCTAAGATCCAGGGAGTTCCTAGGCTCAAATTACAGTGAAACATTCTACTCCATGAAAGGAGGAGCGTTCACCAGGCATCCTCAGATCATG  396
 397 GATCATTGTTTTTACCAAGGATCCATAGTACACGAATATGATTCAGCTGCCAGTATCAGTACGTGTAATGGTCTAAGGGGATTCTTCAGAATAAACGAC  495
 496 CAAAGATACCTCATTGAACCAGTGAAATACTCAGATGAGGGAGAACATTTGGTGTTCAAATATAACCTGAGGGTGCCGTATGGTGCCAATTATTCCTGT  594
 595 ACAGAGCTTAATTTTACCAGAAAAACTGTTCCAGGGGATAATGAATCTGAAGAAGACTCCAAAATAAAAGGCATCCATGATGAAAAGTATGTTGAATTG  693
 694 TTCATTGTTGCTGATGATACTGTGTATCGCAGAAATGGTCATCCTCACAATAAACTAAGGAACCGAATTTGGGGAATGGTCAATTTTGTCAACATGATT  792
 793 TATAAAACCTTAAACATCCATGTGACGTTGGTTGGCATTGAAATATGGACACATGAAGATAAAATAGAACTATATTCAAATATAGAAACTACCTTATTG  891
 892 CGTTTTTCATTTTGGCAAGAAAAGATCCTTAAAACACGGAAGGATTTTGATCATGTTGTATTACTCAGTGGGAAGTGGCTCTACTCACATGTGCAAGGA  990
 991 ATTTCTTATCCAGGGGGTATGTGCCTGCCCTATTATTCCACCAGTATCATTAAGGATCTTTTACCTGACACAAACATAATTGCAAACAGAATGGCACAT 1089
1090 CAACTGGGGCATAACCTTGGGATGCAGCATGACGAGTTCCCATGCACCTGTCCTTCAGGAAAATGCGTGATGGACAGTGATGGAAGCATTCCTGCACTG 1188
1189 AAATTCAGTAAATGCAGCCAAAACCAATACCACCAGTACTTGAAGGATTATAAGCCAACATGCATGCTCAACATTCCATTTCCTTACAATTTTCATGAT 1287
1288 TTCCAATTTTGTGGAAACAAGAAGTTGGATGAGGGTGAAGAGTGTGACTGTGGCCCTGCTCAGGAGTGTACTAATCCTTGCTGTGATGCACACACATGT 1386
1387 GTACTGAAGCCAGGATTTACTTGTGCAGAAGGAGAATGCTGTGAATCTTGTCAGATAAAAAAAGCAGGGTCCATATGCAGACCGGCGAAAGATGAATGT 1485
1486 GATTTTCCTGAGATGTGCACTGGCCACTCGCCTGCCTGTCCTAAGGACCAGTTCAGGGTCAATGGATTTCCTTGCAAGAACTCAGAAGGCTACTGTTTC 1584
1585 ATGGGGAAATGTCCAACTCGTGAGGATCAGTGCTCTGAACTATTTGATGATGATGCAATAGAGAGTCATGATATCTGCTACAAGATGAATACAAAAGGA 1683
1684 AATAAATTTGGATACTGCAAAAACAAGGAAAACAGATTTCTTCCCTGTGAGGAGAAAGATGTCAGATGTGGAAAGATCTACTGCACTGGAGGGGAGCTT 1782
1783 TCCTCTCTCCTTGGAGAAGACAAGACTTATCACCTTAAGGATCCCCAGAAGAATGCTACTGTCAAATGCAAAACTATTTTTTTTATACCATGATTCTACA 1881
1882 GACATTGGCCTGGTGGCGTCAGGAACAAAATGTGGAGAGGGAATGGTGTGCAACAATGGTGAATGTCTAAACATGGAAAAGGTCTATATCTCAACCAAT 1980
1981 TGCCCCTCTCAGTGCAATGAAAATCCTGTGGATGGCCACCGGACTCCAGTGCCACTGTGAGGAAGGACAGGCACCTGTAGCCTGTGAAGAAACCTTACAT 2079
2080 GTTACCAATATCACCATCTTGGTTGTTGTGCTTGTCCTGGTTATTGTCGGTATCGGAGTTCTTATACTATTAGTTCGTTACCGAAAATGTATCAAGTTG 2178
2179 AAGCAAGTTCAGAGCCCACCTACAGAAACCCTGGGAGTGGAGAACAAAGGATACTTTGGTGATGAGCAGCAGATAAGGACTGAGCCAATCCTGCCAGAA 2277
2278 ATTCATTTCCTAAATAGAACTCCAGAATCCTTGGAAAGCCTGCCCACTAGTTTTTCAAGTCCCCACTACATCACACTGAAACCTGCAAGTAAAGATTCA 2376
2377 AGAGGAATCGCAGATCCCAATCAAAGTGCCAAGTGAGCTTGAAGTTGGATATCCAAAATGGCCGTGCAAGCTTAGGCTGGGGATTCTGGATGCAACGTC 2475
2476 TTTACAACCTTACCTAGATATCTGCTACTCACATTTTTGGTAGTGTTTCAAACGTTCTTTATCCAGACAGACAATGTTTAAGAGAAACAACTTATTTCT 2574
2575 GTTAATATTTACCGGTAGAATTCACACCCTCTATCATAAACATATGCTGCAGAAAAAAAA <-β form
                                                                <- α form->TGTCTTGTGGTCTTTCAAATGCTCTTTAGCACAATATAA 2673
2674 AAATTCGTAACCTTGCTGTAGTATTTTCCTACAAAATGTTACTCTGCTTTCTTTAAGAATCCAAACTTTAAGGATGATAACTTACAGTCTAAGAAGAA 2772
2773 AACATTGCATATAAAAAGTTACTTTTTTGGAAACATAAAAGTACGTTTTAAAACTTGAACATGACATCATTAGCACTAATTCTGGTTTAAATGAAAGTC 2871
2872 CTGCAGAAATGCCAAAGAAGGCAGGGCAGGCGGCACGGATTCTAGGTAATTAAAAGTGAAAGAGGCAGAAGAATAGTGGACAGAACTGCAGGATAGTC 2970
2971 CTTAAAATAATGGTGGTGGGAAAGGAAAACACAGAATGCTCCTGGCAATTCTAAATTCCTAGGTTTGCCTTTCTAGAATTCCTTAAGAAGCTGACAGAG 3069
3070 AAATCAGAGGGTTACAAGAATTTTCAGAAAATTTACTCCAAGTGAGAGGACATACTCACAACTCCTATGAAGGGTTTCTAAGGTCTTTGTCCTGTGCAAT 3168
3169 TTGACAATGTGCCATTTCTGTGCTGTCTCTGCCCTCTCCCTATCCGTTTGTTATGGGATGGGGGGTTACCCTGGGAATGATTTCAGCTGCTTCTTACAC 3267
3268 AGATGCCTCTCAAGGTGTTCTTTTGTGTCCTCTATTTTCTTCTTGTGAACTGTTAAAGCTACATGCATTATTTTTTTTCCATTTACTGAAATAAAGTTT 3366
3367 TCAAGTTCTAAATAAAAATGTTCTGACTCGATGAAATAAATAAAGGCTACAAAAGAAGGAAGAAAAAAAAAAAAAAAAAAAAAAAA              3451
```

SEQ ID NO: 1

FIGURE 1 h-ADAM 7 SEQ ID NO: 2

FIGURE 2

```
gatccctgcagtggaagtgaggaggaagaaaggtgaactcctttcctcaagcacttctgc
tctcctctaccagaatcactcagaatgcttcccgggtgtatattcttgatgattttactc
attcctcaggttaaagaaaagttcatccttggagtagagggtcaacaactggttcgtcct
aaaaagcttcctctgatacagaagcgagatactggacacacccatgatgatgacatactg
aaaacgtatgaagaagaattgttgtatgaaataaaactaaatagaaaaacctagtcctt
catcttctaagatccaggagttcctaggctcaaattacagtgaaacattctactccatg
aaaggaggagcgttcaccaggcatcctcagatcatggatcattgttttaccaaggatcc
atagtacacgaatatgattcagctgccagtatcagtacgtgtaatggtctaaggggattc
ttcagaataaacgaccaaagatacctcattgaaccagtgaaatactcagatgagggagaa
catttggtgttcaaatataacctgagggtgccgtatggtgccaattattcctgtacagag
cttaatttaccagaaaaactgttccaggggataatgaatctgaagaagactccaaaata
aaaggcatccatgatgaaaagtatgttgaattgttcattgttgctgatgatactgtgtat
cgcagaaatggtcatcctcacaataaactaaggaaccgaattgggaatggtcaatttt
gtcaacatgattaataaaccttaaacatccatgtgacgttggttggcattgaaatatgg
acacatgaagataaaatagaactatattcaaatatagaaactaccttattgcgtttttca
ttttggcaagaaaagatccttaaaacacggaaggattttgatcatgttgtattactcagt
gggaagtggctctactcacatgtgcaaggaatttcttatccaggggtatgtgcctgccc
tattattccaccagtatcattaaggatcttttacctgacacaaacataattgcaaacaga
atggcacatcaactggggcataaccttgggatgcagcatgacgagtcccatgcacctgt
cctccaggaaaatgcgtgatggacagtgatggaagcattcctgcactgaaattcagtaaa
tgcagccaaaaccaataccaccagtacttgaaggattataagccaacatgcatgctcaac
attccatttccttacaatttctcatgatttccaattttgtggaaacaagaagttggatgag
ggtgaagagtgtgactgtggccctgctcaggagtgtactaatccttgctgtgatgcacac
acatgtgtactgaagccaggatttacttgtgcagaaggagaatgctgtgaatcttgtcag
ataaaaaaagcagggtccatatgcagaccggcgaaagatgaatgtgattttcctgagatg
tgcactggccactcgcctgcctgtcctaaggaccagttcagggtcaatggattttccttgc
aagaactcagaaggctactgtttcatggggaaatgtccaactcgtgaggatcagtgctct
gaactatttgatgatgatgcaatagagagtcatgatatctgctacaagatgaatacaaaa
ggaaataaatttggatactgcaaaaacaaggaaaacagatttcttccctgtgaggagaaa
gatgtcagatgtggaaagatctactgcactggaggggagctttcctctctccttggagaa
gacaagacttatcaccttaaggatccccagaagaatgctactgtcaaatgcaaaactatt
ttttataccatgattctacagacattggcctggtggcgtcaggaacaaaatgtggagag
ggaatggtgtgcaacaatggtgaatgtctaaacatggaaaaggtctatatctcaaccaat
tgcccctctcagtgcaatgaaaatcctgtggatggccacggactccagtgccactgtgag
gaaggacaggcacctgtagcctgtgaagaaaccttacatgttaccaatatcaccatcttg
gttgttgtgcttgtcctggttattgtcggtatcggagttcttatactattagttcgttac
cgaaaatgtatcaagttgaagcaagttcagagcccacctacagaaacctgggagtggag
aacaaaggatactttggtgatgagcagcagataaggactgagccaatcctgccagaaatt
catttcctaaatagaactccagaatccttggaaagcctgcccactagttttcaagtccc
cactacatcacactgaaacctgcaagtaaagattcaagaggaatcgcagatcccaatcaa
agtgccaagtgagcttgaagttggatatccaaaatggccgtgcaagcttaggctggggat
tctggatgcaacgtctttacaaccttacctagatatctgctactcacattttggtagtg
tttcaaacgttctttacccagacagacaatgtttaagagaaacaacttatttctgttaat
atttaccggtagaattcacaccctctatcataaacatatgctgcagaaaaaaaatgtctt
gtggtctttcaaatgctctttagcacaatataaaaattcgtaaccttgctgtagtatttt
cctacaaaatgttactctgctttcttttaagaatccaaactttaaggatgataacttaca
gtctaagaagaaaacattgcatataaaaagttactttttgaaacataaaagtacgttt
taaaacttgaacatgacatcattagcactaattctggttaaatgaaagtcctgcagaaa
tgccaaagaaggcagggcagagcggcacggattctaggtaattaaaagtgaaagaggcag
aagaatagtggacagaactgcaggatagtccttaaaataatggtggtgggaaggaaaac
acagaatgctcctggcaattctaaattcctaggtttgcctttctagaattccttaagaag
ctgacagagaaatcagagggttacaagaatttcagaaaatttactccaagtgagaggaca
tactcacaactcctatgaagggtttctaaggtctttgtcctgtgcaatttgacaatgtgc
catttctgtgctgtctctgccctctccctatccgtttgttatgggatggggggttaccct
gggaatgatttcagctgcttcttacacagatgcctctcaaggtgttctttttgtgtcctct
atttttcttcttgtgaactgttaaagctacatgcattatttttttccatttactgaaata
aagttttcaagttctaaataaaaatgttctgactcgatg aaataaataa aggctacaa
aagaaggaagaaaaaaaaaaaaaaaaaaaaaaaa
```

FIGURE 3

```
gatccctgcagtggaagtgaggaggaagaaaggtgaactccttttctcaagcacttctgc
tctcctctaccagaatcactcagaatgcttcccgggtgtatattcttgatgattttactc
attcctcaggttaaagaaaagttcatccttggagtagagggtcaacaactggttcgtcct
aaaaagcttcctctgatacagaagcgagatactggacacacccatgatgatgacatactg
aaaacgtatgaagaagaattgttgtatgaaataaaactaaatagaaaaaccttagtcctt
catcttctaagatccagggagttcctaggctcaaattacagtgaaacattctactccatg
aaaggaggagcgttcaccaggcatcctcagatcatggatcattgttttaccaaggatcc
atagtacacgaatatgattcagctgccagtatcagtacgtgtaatggtctaaggggattc
ttcagaataaacgaccaaagatacctcattgaaccagtgaaatactcagatgagggagaa
catttggtgttcaaatataacctgagggtgccgtatggtgccaattattcctgtacagag
cttaattttaccagaaaactgttccaggggataatgaatctgaagaagactccaaaata
aaaggcatccatgatgaaagtatgttgaattgttcattgttgctgatgatactgtgtat
cgcagaaatggtcatcctcacaataaactaaggaaccgaatttggggaatggtcaatttt
gtcaacatgatttataaaaccttaaacatccatgtgacgttggttggcattgaaatatgg
acacatgaagataaaatagaactatattcaaatatagaaactaccttattgcgtttttca
ttttggcaagaaaagatccttaaaacacggaaggattttgatcatgttgtattactcagt
gggaagtggctctactcacatgtgcaaggaatttcttatccagggggtatgtgcctgccc
tattattccaccagtatcattaaggatcttttacctgacacaaacataattgcaaacaga
atggcacatcaactggggcataaccttgggatgcagcatgacgagttcccatgcacctgt
ccttcaggaaaatgcgtgatggacagtgatggaagcattcctgcactgaaattcagtaaa
tgcagccaaaaccaataccaccagtacttgaaggattataagccaacatgcatgctcaac
attccatttccttacaattttcatgatttccaattttgtggaaacaagaagttggatgag
ggtgaagagtgtgactgtggccctgctcaggagtgtactaatccttgctgtgatgcacac
acatgtgtactgaagccaggatttacttgtgcagaaggagaatgctgtgaatcttgtcag
ataaaaaaagcagggtccatatgcagaccggcgaaagatgaatgtgatttcctgagatg
tgcactggccactcgcctgcctgtcctaaggaccagttcagggtcaatggatttccttgc
aagaactcagaaggctactgtttcatggggaaatgtccaactcgtgaggatcagtgctct
gaactatttgatgatgatgcaatagagagtcatgatatctgctacaagatgaatacaaaa
ggaaataaatttggatactgcaaaaacaaggaaaacagatttcttccctgtgaggagaaa
gatgtcagatgtggaaagatctactgcactggaggggagctttcctctctccttggagaa
gacaagacttatcaccttaaggatccccagaagaatgctactgtcaaatgcaaaactatt
tttttataccatgattctacagacattggcctggtggcgtcaggaacaaaatgtggagag
ggaatggtgtgcaacaatggtgaatgtctaaacatggaaaaggtctatatctcaaccaat
tgcccctctcagtgcaatgaaaatcctgtggatggccacggactccagtgccactgtgag
gaaggacaggcacctgtagcctgtgaagaaaccttacatgttaccaatatcaccatcttg
gttgttgtgcttgtcctggttattgtcggtatcggagttcttatactattagttcgttac
cgaaaatgtatcaagttgaagcaagttcagagcccacctacagaaaccctgggagtggag
aacaaaggatactttggtgatgagcagcagataaggactgagccaatcctgccagaaatt
catttcctaaatagaactccagaatccttggaagcctgcccactagttttcaagtccc
cactacatcacactgaaacctgcaagtaaagattcaagaggaatcgcagatcccaatcaa
agtgccaagtgagcttgaagttggatatccaaaatggccgtgcaagcttaggctgggat
tctggatgcaacgtctttacaaccttacctagatatctgctactcacattttggtagt
gtttcaaacgttctttacccagacagacaatgtttaagagaaacaacttatttctgttaat
atttaccggtagaattcacaccctctatcataaacatatgctgcagaaaaaaaa
```

FIGURE 4

NUCLEIC ACID MOLECULES AND POLYPEPTIDES RELATED TO H-ADAM7

The present invention is not sponsored in whole or in part by the United States Government.

BACKGROUND OF THE INVENTION

In mammals, sperms are exposed to a microenvironment created by the absorptive and secretory activities of the epididymal epithelium cells (Cooper, 1998). Passing along the epididymal duct, sperm undergo morphological and functional modifications (Jones, 1998), which culminate in the acquisition of forward motility and the ability to recognize and penetrate the zona pellucida of egg (Cooper, 1990; Liu et. al., 1991; Turner, 1995). Epididymal secretions contain many kinds of proteins including superoxide dismutase (Perry et. al., 1993), peroxidase (Ghyselinck, et. al., 1993), glycosidases (Toshimori et. al., 1988) transport proteins, as well as sperm maturation antigens (Araki et. al., 1992; Mahony et. al., 1994; Weaver et. al., 1993). It is believed that interaction between epididymal secretary proteins and sperm membrane during sperm maturation is required for normal fertility in the male (Myles, 1993). However, the roles of epididymal secretory proteins in sperm maturation are not well defined (Myles, 1993; Cornwall and Hann, 1995).

A novel family of transmembrane proteins that contain a disintegrin and metalloprotease (ADAM) domain had been identified in a variety of tissues and species (Primakoff and Myles, 2000). Total of 29 ADAM cDNAs have been cloned and sequenced (Stone et al., 1999; Primakoff and Myles, 2000). Although the biological functions are not well defined, ADAMs are found involved in rather diverse biological processes, such as virus-cell fusion (Hermandeez et al, 1996), neurogenesis (Schlondorff and Blobel, 1999) and fertilization (Blobel et al, 1992; Bigler et al, 1997). A full-length ADAM cDNA encodes a multi-domain protein containing pro-domain, metalloprotease, disintegrin, cysteine-rich, epidermal growth factor (EGF)-like, transmembrane, and cytoplasmic domains (Wolfsberg et al., 1995 a, b; Primakoff and Myles, 2000). Among the 29 known ADAM cDNAs, 12 are testis-specific and 3 are testis-predominant (Primakoff and Myles, 2000). These 15 ADAMs are proposed to play important roles in spermatogenesis or/and fertilization. The inhibition of sperm-egg fusion by fertilin □ (ADAM2)-specific monoclonal antibody (Primakoff et al, 1987) further substantiates the role of ADAM in fertilization. The ADAM7 molecules found in the rat, monkey (Perry et al, 1992) and mouse (Cornwall and Hsia, 1997) are all epididymis-specific and proposed to be involved in sperm maturation. However, biological functions of ADAMs in sperm maturation and fertilization are not yet defined.

SUMMARY OF THE INVENTION

The present invention is based on the discovery of genes encoding a human epididymis-associated disintegrin and metalloprotease 7 protein (GP-83). The identity of GP-83-encoding cDNA was determined by searching the GenBank and EMBL Data Banks, which revealed sequence homology to the metalloprotease and disintegrin domains of ADAM molecules (see, e.g., Wolfsberg et al. (1995) J Cell Biol 131:275–278; Wolfsberg et al. (1995) Dev Biol 169:378–383). The cDNA sequence of GP-83 exhibited significant sequence homology to EAP-1 of monkey and rat (see, e.g., Perry et al. (1992) Biochem J 286:671–675) and ADAM 7 of mouse (see, e.g. Cornwall and Hsia (1997) Endocrinology 138: 4262–4272) (see FIG. 2). Therefore, these molecules are referred to as ADAM7 of human, monkey, rat and mouse respectively. Blasting in NCBI, the nucleotide sequence encoding ADAM 7 of human (h-ADAM7) was mapped to chromosome 8p22 according to the DNA sequences elucidated by the Human Genome Project.

Both Northern blotting and immunoblotting (Sun et al, 2000) demonstrated that GP-83 was expressed in human epididymis, but not in testis. These results further indicate that all ADAM7 proteins identified to date are all expressed by epididymal epithelial cells (Wolfsberg and White, 1996). Although the biological roles of ADAM7 proteins are not defined yet, putative protease and adhesion domains imply roles in cell-cell interaction, protein processing and cell signaling (Cornwall and Hsia, 1997). Our previous studies demonstrated that GP-83 secreted by human epididymis was found on anterior acrosome of ejaculated sperm and equatorial region of acrosome-reacted sperm (Sun et al., 2000). These findings suggest that ADAM7 may be involved in sperm maturation and sperm-egg interaction.

There are two isoforms of h-ADAM7 (see FIG. 1), i.e. the α and β forms of 3451 bp (SEQ ID NO: 1) and 2463 bp (SEQ ID NO: 3) respectively. Both cDNA sequences exhibit an open reading frame of 2262 bp, predicting a peptide of 754 amino acid residues (SEQ ID NO: 2). The encoded GP-83 protein contains a signal sequence, a prodomain (169 residues), a metalloprotease domain (204 residues, encoded by SEQ ID NO: 4), a disintegrin domain (91 residues, encoded by SEQ ID NO: 5), a cysteine-rich domain (141 residues), a EGF-like domain (29 residues), a transmembrane domain and a cytoplasmic domain (64 residues and 39 residues respectively encoded by nucleotide sequence of SEQ ID NO: 6).

In most ADAMs, the pro-protein domain is cleaved off to activate the protease domain. The regulation mechanism, as found in the soluble matrix metalloprotease (MMPs) and crotalid snake venom metalloprotease (SVMPs), is referred as "cysteine switch" (Van Wart and Birkedal-Hansen, 1990; Grams et al., 1993). Due to the presence of an unpaired cysteine, cysteine switch is thought to interact with $Zn^{2+}$ in the catalytic domain. However, the metalloproteinase catalytic residue, the glutamate (E) is replaced by a glutamine (Q) in h-ADAM7 and other ADAM7 proteins. Thus, h-ADAM7 protein may not have protease activity as Cornwall and Hsia (1997) proposed for other ADAM proteins.

ADAMs display structural homology to snake venom metalloprotease (SVMPs) and are postulated to function as adhesive protein ligands such as fibronectin, vitronectin and fibrinogen (Hynes, 1987). The disintegrin of SVMPs after proteolytic processing are integrin ligands of 50–80 amino acids. These disintegrins interact with integrins through a thirteen amino acid motif that contains an integrin-binding sequence, RGD (Arg-Gly-Asp). The disintegrin-like domains of some or all ADAMs are likely ligands for integrins or other receptors (Wolfsberg and White, 1996). Instead of the RGD-cell binding motif present in SVMP disintegrins, ADAM 15 (metargidin) is the only ADAM that expresses RGD (Krätzschmar et al., 1996; Herren et al., 1997). The disintegrin domain of h-ADAM7 contains a unique KDE sequence. Although the disintegrin domain of h-ADAM7 shares 86% identity with that of the monkey ADAM7 (EAP-I), the tripeptide sequence of EAP-I is EDE (Perry et al, 1992). It is not clear if the difference in tripeptide sequence of ADAM7 disintegrin is due to integrin-disintegrin specificity or species-specificity of sperm-egg interactions.

Cytoplasmic tails of the ADAMs, ranging from 11 to 176 amino acids in length, do not share significant sequence similarity with each other or with other proteins. Several ADAMs tails are rich in poline, which suggests that they may contain binding sites for cytoskeleton-associated proteins or SH3 domain-containing proteins, a large group of molecules involving cell signaling. The intracellular domain of h-ADAM7 contains SH3 consensus sequences, RTEPILP (Alexandropoulos et al., 1995; Pawson, 1995; Wolfsberg and White, 1996). These findings suggest that signal transduction may be involved in h-ADAM7 (GP-83)-mediated sperm maturation and fertilization.

The present invention features a nucleic acid molecule which is at least about 50% (or 60%, 70%, 80%, 90%, or 95%) identical to the nucleotide sequence shown in SEQ ID NO: 1, SEQ ID NO: 3, SEQ ID NO: 4, SEQ ID NO: 5, and SEQ ID NO: 6 or a complement thereof.

The invention also encompasses a nucleic acid molecule that encodes polypeptides with an amino acid sequence of at least about 50% (70%, 90%, 95%, 96%, 97%, 98%, or 99%) identical to SEQ ID NO: 2 or a complement thereof.

The invention also features nucleic acid molecules that hybridizes under stringent conditions to SEQ ID NO: 1 or a fragment thereof of at least about 100 (300, 800, 1000, 2,000, 2,500 or 3,000) nucleotides in length.

Also included in the invention is a nucleic acid molecule that encodes SEQ ID NO: 2 or a fragment thereof that is at least about 5 (10, 30, 60, 80, 150, 200, or 250) residues in length.

The invention encompasses purified polypeptide that the amino acid sequence of which comprises at least 20, 30, 50, 70, 100, 200, 400, or 600 consecutive residues of SEQ ID NO: 2.

Also within the invention is a purified polypeptide that is at least about 50% (65%, 75%, 85%, 95%, 96%, 97%, 98%, or 99%) identical to SEQ ID NO: 2.

Another aspect of the invention provides a vector, e.g., a recombinant expression vector comprising GP-83 nucleic acid molecules of the invention. Also, included in the invention is the host cell into which the recombinant expression vector has been introduced and the product of the recombinant expression vector, e.g., the recombinant GP-83 polypeptide.

The invention further features antibodies that specifically bind GP-83 protein.

The invention also includes assay for test compounds that modulates activities of GP-83 protein.

BRIEF DESCRIPTION OF THE DRAWINGS

FIG. 1 depicts the α and β forms of GP-83-encoding cDNA sequences and the corresponding amino acid sequence of GP-83.

FIG. 2 depicts a comparison of amino acid sequences derived from cDNA sequence of h-ADAM 7 (SEQ ID NO: 2) and related proteins from other species. The amino acid sequences of the related proteins are mfeapi (SEQ ID NO: 7). r-ADAM7 (SEQ ID NO: 8). m-ADAM7 (SEQ ID NO: 9). ADAM2 (SEQ ID NO: 10). SMVP (SEQ ID NO: 11).

FIG. 3 depicts the α form of h-ADAM7 cDNA sequence (SEQ ID NO: 1).

FIG. 4 depicts the β form of h-ADAM7 cDNA sequence (SEQ ID NO: 3).

DETAILED DESCRIPTION OF THE INVENTION

Figure 5:
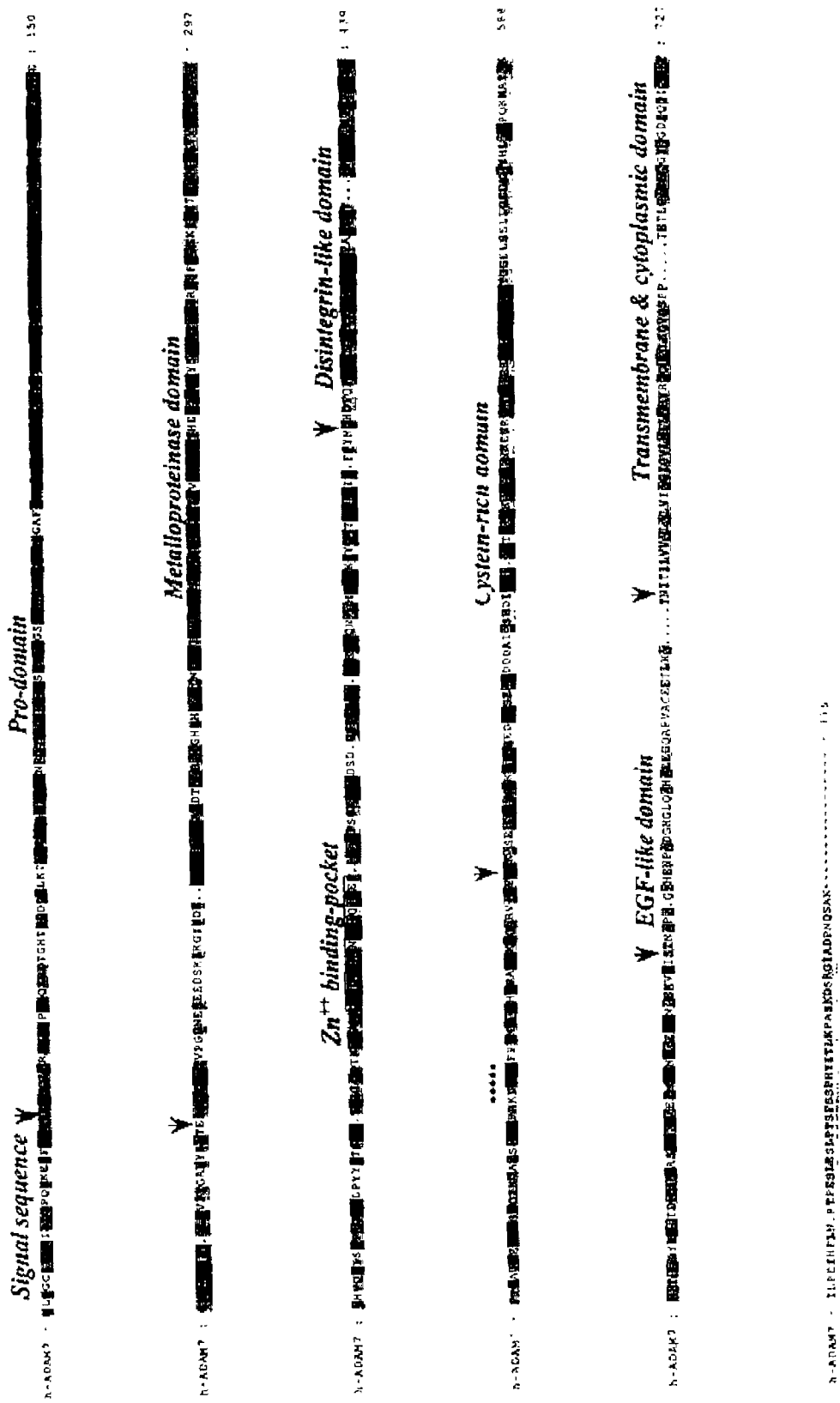
FIG. 5 depicts the predicted amino acid sequence of a GP-83 protein (SEQ ID NO: 2) and its respective domains

The present invention is based on the discovery of a cDNA molecule (h-ADAM7) that encodes a human epididymis-associated disintegrin and metalloprotease 7 protein, a glycoprotein of 83 kDa (GP-83). There are two isoforms of the GP-83-encoding cDNA sequences; one is of 3451 bp (α form) (see FIG. 3) and the other is of 2463 bp (β form) (see FIG. 4) including the poly (A) tail. Because the segment of 2411–3451 bp in α form was an untranslated region, both cDNA sequences exhibit an open reading frame of 2262 bp, predicting a peptide of 754 amino acid residues (see FIG. 5). The nucleotide sequence of both the α and β forms of GP-83-encoding cDNA sequences is shown in FIG. 3 (SEQ ID NO: 1) and FIG. 4 (SEQ ID NO: 2) respectively. The predicted amino acid sequence of GP-83 protein is also shown in FIG. 5 (SEQ ID NO: 3).

As used interchangeably herein "biological activity of GP-83" and "GP-83 activity" refers to an activity exerted by a GP-83 protein, polypeptide or nucleic acid molecule on a GP-83 responsive cell, which activity can be determined in vivo or in vitro according to standard techniques. A GP-83 activity can be a direct activity, such as an association with or an enzymatic activity on a second protein, or an indirect activity, such as a cellular signaling mediated by interaction of GP-83 protein with a second protein. In a preferred embodiment, a GP-83 activity includes at least one or more of the following activities: (i) interaction with sperm in the epididymis (ii) interaction with GP-83 ligands (iii) interaction with intracellular target proteins, (iv) binds integrin in specific integrin-disintegrin interactions, (v) mediate signal transduction, (vi) interaction with oocyte in sperm-oocyte fertilization.

I. Isolated Nucleic Acid Molecules

The present invention relates to isolated nucleic acid molecules that encode GP-83 protein or biologically active portions thereof, as well as nucleic acid molecules that differ from the GP-83 encoding nucleic acid molecule due to degeneracy of the genetic code and thus encode the same GP-83 protein. The term "nucleic acid molecules" as used herein include DNA molecules (e.g., cDNA or genomic DNA) and RNA molecules (e.g., mRNA, rRNA) and analogs of the DNA or RNA generated using nucleotide analogs. The nucleic acid molecule can be single-stranded or doubled-stranded, but preferably is double-stranded DNA.

An "isolated" nucleic acid molecule is one which is separated from other nucleic acid molecules which are present in the natural source of the nucleic acid. Preferably, an isolated nucleic acid molecule is free of sequences which naturally flank the nucleic acid, such as sequences at the 5' and 3' ends of the nucleic acid, in the genomic DNA of the organism from which the nucleic acid is derived. For example, in various embodiments, the isolated GP-83-encoding nucleic acid molecule can contain less than 5 kb, 4 kb, 3 kb, 2 kb, 1 kb, 0.5 kb, and 0.1 kb of nucleotide sequences which naturally flank the nucleic acid molecule in genomic DNA of the cell from which the nucleic acid is derived. Also, an "isolated" nucleic acid molecule, such as a cDNA molecule, can be substantially free of other cellular material or culture medium when produced by recombinant techniques and substantially free of other chemical precursors when chemically synthesized.

A nucleic acid molecule of the present invention, i.e. nucleic acid molecules with nucleotide sequences shown in SEQ ID NO: 1, SEQ ID NO: 3, SEQ ID NO: 4, SEQ ID NO: 5 and SEQ ID NO: 6, or a complement of any of these nucleotide sequences, can be isolated using standard molecular biology techniques and the sequence information provided herein. Using all or a portion of the nucleic acid sequences of in SEQ ID NO: 1, SEQ ID NO: 3, SEQ ID NO: 4, SEQ ID NO: 5 and SEQ ID NO: 6 as a hybridization probe, GP-83-encoding nucleic acid molecules can be isolated employing standard hybridization and cloning techniques (e.g. as described in Sambrook et al., eds., *Molecular Cloning: A Laboratory Manual*. $2^{nd}$, ed., Cold Spring Harbor Laboratory, Cold Spring Harbor Laboratory Press, Cold Spring Harbor, N.Y. 1989).

A nucleic acid molecule of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to GP-83 nucleotide sequence can be prepared by standard synthetic techniques, such as using an automated DNA synthesizer.

Furthermore, the present invention can comprise only a portion of a nucleic acid sequence encoding GP-83, for example, fragments sufficient for use as hybridization probes to identify GP-83-encoding nucleic acids, such as a GP-83 mRNA, fragments for use as PCR primers for the amplification or mutation of GP-83 nucleic acid molecules, or fragments encoding a biologically active portion of GP-83. The nucleotide sequence determined from the cloning of the human GP-83 gene allows for the generation of probes and primers designed for use in identifying and/or cloning GP-83 homologues e.g., GP-83 homologues from other mammals. The probe/primer typically comprises substantially purified oligonucleotide. The oligonucleotide typically comprises a region of nucleotide sequence that hybridizes under stringent conditions to at least about 10, preferably about 20, 30, 40, 50, 60, 70, or 80, more preferably about 100, 200, 300, 400, 500, or 600 consecutive nucleotides of the sense or antisense of SEQ ID NO: 1, SEQ ID NO: 3, and SEQ ID NO: 4, about 100, 200, or 250 consecutive nucleotides of the sense or antisense of SEQ ID NO: 5 and SEQ ID NO: 6 or a naturally occurring mutant of SEQ ID NO: 1, SEQ ID NO: 3, SEQ ID NO: 4, SEQ ID NO: 5, and SEQ ID NO: 6.

Probes based on human GP-83 nucleotide sequence can be used to detect transcripts or genomic sequences encoding the same or identical proteins. The probe usually comprises a label group attached thereto, e.g., a radioisotope, a fluorescent compound, an enzyme, or an enzyme co-factor. Such probes can be used as a part of a diagnostic test kit for identifying cells or tissue which mis-express GP-83 proteins, such as by measuring the level of a GP-83-encoding nucleic acids in a sample of cells from the subjects. For example, the level of GP-83 mRNA in a given tissue sample can be determined or determining whether the genomic GP-83 gene has been mutated or deleted.

A nucleic acid fragment encoding a "biologically active portion of GP-83" can be prepared by isolating a portion of SEQ ID NO:1, SEQ ID NO: 3, SEQ ID NO: 4, SEQ ID NO: 5, and SEQ ID NO: 6 which encodes a polypeptide having a GP-83 activity, expressing the encoded PG-83 protein, such as by recombinant expression in vitro, and assessing the activity of the encoded portion of GP-83. For example, a nucleic acid fragment encoding a biologically active portion of GP-83 includes a disintegrin domain and or a metalloprotease domain.

In another preferred embodiment, an isolated nucleic acid molecule of the invention comprises a nucleic acid molecule which is a complement of the nucleotide sequence of SEQ ID NO:1, SEQ ID NO: 3, SEQ ID NO: 4, or a portion thereof. A nucleic acid molecule which is complementary to the given nucleotide sequence is one which is sufficiently complementary to the given nucleotide sequence that it can hybridize to the given nucleotide sequence thereby forming a stable duplex.

In addition to the nucleotide sequence shown in SEQ ID NO: 1, SEQ ID NO: 3, SEQ ID NO: 4, and SEQ ID NO 5, it will be appreciated by those skilled in the art that DNA sequence polymorphisms that lead to changes in the amino acid sequences of GP-83 may exist within a population, such as the human population. Such genetic polymorphism of GP-83 gene may exist among individuals within a population due to natural allelic variation. As used herein, the terms "gene" and "recombinant gene" refer to nucleic acid molecules comprising an open reading frame encoding a GP-83 protein, preferably a mammalian GP-83 protein. Such natural allelic variations can typically result in 1–5% variance in the nucleotide sequence of a GP-83 gene. Any and all such nucleotide variations and resulting amino acid polymorphisms in GP-83 that are the result of natural allelic variation and that do not alter the activity of GP-83 are intended to be within the scope of the invention.

Accordingly, in another embodiment, an isolated nucleic acid molecule of the invention is at least 300, 400, 500, 600, 700, 800, 900, 1000, 1100, 1200, 1300, 1400, 1500, 1600, 1700, 1800, 1900, 2100, and 2200 nucleotides in length and hybridize under stringent conditions to the nucleic acid molecule comprising preferably the coding sequence of SEQ ID NO: 1, SEQ ID NO: 3, SEQ ID NO: 4, and SEQ ID NO 5.

The term "stringent condition", as used herein, describes conditions for hybridization and washing under which nucleotide sequences at least 60% (80%, 90% preferably 95%) identical to each other typically remained hybridized to each other. Such stringent conditions are known to those skilled in the art and can be found in *Current Protocols in Molecular Biology*, John Wiley & Sons, N.Y. (1989), 6.3.1–6.3.6. Melting temperature, i.e., the temperature at which a probe disassociates from a target DNA, is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE). Then assuming that 1% mismatching results in a 1° C. decrease in the melting temperature, the temperature of the final wash in the hybridization reaction is reduced accordingly (for example, if sequences having >95% identity with the probe are sought, the final wash temperature is decreased by 5° C.). In practice, the change in melting temperature can be between 0.5° C. and 1.5° C. per 1% mismatch. Stringent conditions involve hybridizing at 68° C. in 5×SSC/5× Senhardt's solution/1.0% SDS, and washing in 0.2×SSC/0.1% SDS at room temperature. Preferably, an isolated nucleic acid molecule of the invention that hybridizes under stringent conditions to the sequence of SEQ ID NO: 1, SEQ ID NO: 3, SEQ ID NO: 4,SEQ ID NO: 5, and SEQ ID NO: 6 corresponds to a "naturallyoccurring" nucleic acid molecule The term "naturally occurring" nucleic acid molecule refers to an RNA or DNA molecule having a nucleotide sequence that occurs in nature (e.g., encoding a natural protein).

In addition to naturally-occurring allelic variants of a GP-83 gene that may exist in the population, these skilled in the art will further appreciate that changes can be introduced, by mutation, into the nucleotide sequence of SEQ ID NO: 1, SEQ ID NO: 3, SEQ ID NO: 4, SEQ ID NO: 5, and SEQ ID NO: 6, thereby leading changes in the amino acid sequence of the encoded GP-83 protein, without altering the functional ability of a GP-83 protein. For example, one can make nucleotide substitutions leading to amino acid substitutions at "nonessential" amino acid residues. A "nonessential" amino acid residue is a residue that can be altered from the wild-type sequence of GP-83 (e.g., the sequence of SEQ ID NO: 1, SEQ ID NO: 3, SEQ ID NO:4, SEQ ID NO: 5, and SEQ ID NO: 6) without altering the biological activity of GP-83 protein. Whereas, an "essential" amino acid residue is required for biological activity. For example, amino acid residues that are conserved among GP-83 proteins of various species are predicted to be particularly unamenable to alteration.

For example, preferred GP-83 protein of the present invention contains at least a pro-domain, a metalloproteinase domain, a disintegrin domain, and a cystein-rich domain. Such conserved domains are less likely to be amenable to mutation. Other amino acid residues, i.e. those that are conserved or semi-conserved among the species, may not be essential for activity and thus are likely to be amenable to alterations.

Accordingly, another aspect of the present invention relates to nucleic acid molecule encoding a GP-83 protein that contains changes in amino acid residues that are not essential for activity. Such GP-83 protein differ in amino acid sequence from SEQ ID NO: 2 and yet retain its biological activity. In one embodiment, the isolated nucleic acid molecule includes a nucleotide sequence encoding a protein that includes amino acid sequence that is at least about 50%, 55%, 60%, 65%, 70%, 75%, 80%, 85%, 90%, 95%, 96%, 97%, 98%, or 99% identical to the amino acid sequence of SEQ ID NO:2.

An isolated nucleic acid molecule encoding a GP-83 protein having a sequence which differs from that of SEQ ID NO: 2 can be created by introducing on or more nucleotide substitutions, additions, or deletions into the nucleotide sequence of SEQ ID NO: 1, SEQ ID NO:3, SEQ ID NO: 4, SEQ ID NO: 5, and SEQ ID NO: 6 such that one or more amino acid substitutions, additions or deletions are introduced into the encoded protein. Mutations can be introduced by standard techniques, such as site-directed mutagenesis and PCR mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted nonessential amino acid residue in GP-83 is preferably replaced with another amino acid residue from the same side chain family. Alternatively, mutations can be introduced randomly along all or part of a GP-83 coding sequence such as by saturation mutagenesis, and the resultant mutant can be screened for GP-83 biological activity to identify mutants that retain activity. Following mutagenesis, the encoded protein can be expressed recombinantly and the activity of the protein can be determined.

In a preferred embodiment, a mutant GP-83 can be assayed for (i) the ability to bind to sperms in epididymis, (ii) the ability to bind a GP-83 ligand, or (iii) the ability to bind to an intracellular target protein.

The present invention relates to antisense nucleic acid molecules, i.e., molecules which are complementary to sense nucleic acid encoding a protein, for example, complementary to the coding strand of a double-stranded cDNA molecule or complementary to an mRNA sequence. Accordingly, an antisense nucleic acid can hydrogen bond to a sense nucleic acid. The antisense nucleic acid can be complementary to the entire GP-83 coding strand, or to only portion thereof, e.g., all or part of the protein coding region or open reading frame. Furthermore, an antisense nucleic acid molecule can be antisense to noncoding region of the coding strand of a nucleotide sequence encoding a GP-83 protein. The noncoding regions, i.e., untranslated 5' and 3' ends, are the 5' and 3' sequences which flank the coding region and are not translated into amino acids.

Given the coding strand sequences encoding GP-83 disclosed herein, i.e., SEQ ID NO: 1, SEQ ID NO: 4, SEQ ID NO: 5, and SEQ ID NO: 6, antisense nucleic acid of the invention can be designed based on the base pairing rules of Watson and Crick. The antisense nucleic acid molecule can be complementary to the entire coding region of GP-84 mRNA, but more preferably is an oligonucleotide which is antisense to only a portion of the coding or noncoding region of a GP-83 mRNA. For example, the antisense oligonucleotide can be complementary to the region surrounding the translation start site of GP-83 mRNA or the region within the active site of the metalloprotease domain, the binding motif of the disintegrin domain and the transmembrane and cytoplasmic domain. An antisense oligonucleotide can be, for example, about 5, 10, 20, 25, 30, 35, 40, 45, or 50 nucleotides in length. An antisense nucleic acid of the present invention can be constructed using chemical synthesis and enzymatic ligation reactions using procedures known in the art. For example, an antisense nucleic acid can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modifie nucleotides which can be used to generate the antisense nucleic acids include 5-fluororacil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carbosymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcysteine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosne, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation, i.e., RNA transcribed from the inserted nucleic acid will be of an antisense orientation to a target nucleic acid of interest.

The antisense nucleic acid molecules of the invention are typically administered to a subject or generated in situ such that they hybridize with or bind to cellular mRNA and/or genomic DNA encoding a GP-83 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes. Ribozymes are catalytic RNA molecules with ribonuclease activity which are capable of cleaving a single-stranded nucleic acid such as an mRNA, to which they have a complementary region. Thus, ribozymes (e.g., hammerhead ribozymes described in Haselhoff and Gerlach (1988) nature 334: 585–591) can be used to catalytically cleave GP-83 mRNA transcripts to thereby inhibit translation of GP-83 mRNA. A ribozyme having specificity for a GP-83-encoding nucleic acid can be designed based upon the nucleotide sequence of GP-83 cDNA disclosed in SEQ ID NO: 1. For example, a derivative of a Tetrahymena L-19 IVS RNA can be constructed in which the nucleotide sequence of the active site is complementary to the nucleotide sequence to be cleaved in a GP-83-encoding mRNA, see e.g., Cech et al. U.S. Pat. No. 4,987,071 and Cech et al. U.S. Pat. No. 5,116,742. Alternatively, GP-83 mRNA can be used to select a catalytic RNA having a specific ribonuclease activity from a pool of RNA molecules, see e.g., Bartel and Szostak (1993) *Science* 261:1411–1418.

The invention also encompasses nucleic acid molecule which forms triple helical structures. For example, GP-83 gene expression can be inhibited by targeting nucleotide sequences complementary to the regular region of GP-83-encoding gene to form triple helical structures that prevent transcription of a GP-83 gene in target cells. See generally, Helene (1991) *Anticancer Drug Des.* 6(6):569–84; Helene (1992) *Ann. N.Y. Acad. Sci.* 660:27–36; and Maher (1992) Bioassays 14(12): 807–15.

In preferred embodiments, the nucleic acid molecules of the invention can be modified at the base moiety, sugar moiety or phosphate backbone to improve, e.g., the stability hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4(1): 5–23). As used herein, the terms "peptide nucleic acids" or "PNAs" refer to nucleic acid mimics, e.g., DNA mimics, in which the deoxyribose phosphate backbone is replaced by pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-Okeefe et al. (1996) *Proc. Natl. Acad. Sci. USA* 93: 14670–675.

PNAs of GP-83 can be used in therapeutic and diagnostic applications. For example, PNAs can be used as antisense or antigene agents for sequence specific modulation of gene expression by e.g., inducing transcription or translation arrest or inhibiting replication. PNAs of GP-83 can also be used, e.g., in the analysis of single base pair mutations in a gene by, e.g., PNA directed PCR clamping; as artificial restriction enzymes when used in combination with other enzymes, e.g., SI nucleases (Hyrup (1996) supra; or as probes or primers for DNA sequence and hybridization (Hyrup (1996) supra; Perry-O'Keefe et al. (1996) *Proc. Ntl. Acad. Sci. USA* 93: 14670–675).

In another embodiment, PNAs of GP-83 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of GP-83 can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) supra). The synthesis of PNA-DNA chimeras can be performed as described in Hyrup (1996) supra and Fin et al. (1996) *Nucleic Acids Research* 24(17):3357–63. For example, a DNA chain can by synthesized on a solid support using standard phosphoramidite coupling chemistry and modified nucleoside analogs, e.g., 5'-4(-methoxytrityl)amino-5'-deoxy-thymidine phosophoramidite, can be used as a between the PNA and the 5' end of DNA (Mag et al. (1989) *Nucleic Acid Res.* 17:5973–88). PNA monomers are then coupled in a stepwise manner to produce a chimeric molecule with a 5' PNA segment and a 3' DNA segment (Finn et al. (1996) *Nucleic Acids Research* 24 (17):3357–63). Alternatively, chimeric molecules can by synthesized with a 5' DNA segment and a 3' PNA segment (Peterser et al. (1975) *Bioorganic Med. Chem. Lett.* 5:1119–1124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT publication No. WO 88/09810) or the blood-brain barrier (see, e.g., PCT Publication NO. WO 89/10134). In addition, oligonucleotides can be modified with hybridization-triggered cleavage agents (see, e.g., Krol et al. (1988) *Bio/Techniques* 6:958–976) or intercalating agents (see, e.g., Zon (1988) *Pharm. Res.* 5:539–549). To this end, the oligonucleotide may be conjugated to another molecule, e.g., a peptide, hybridization triggered cross-linking agent, transport agent, hybridization-triggered cleavage agent etc.

II. Isolated GP-83 Proteins and Anti-GP-83 Antibodies

The present invention also relates to purified GP-83 proteins and biologically active portions thereof, as well as polypeptide fragments suitable for use as immunogens to raise anti-GP-83 antibodies. In one embodiment, native GP-83 proteins can be isolated from cells, tissues, or body fluid sources by an appropriate purification scheme using standard protein purification techniques. In another embodiment, GP-83 proteins are produced by recombinant DNA techniques. Alternative to recombinant expression, a GP-83 protein or polypeptide can be synthesized chemically using standard peptide synthesis techniques.

An "isolated" or "purified" protein or biologically active portion thereof is substantially free of cellular material on other contaminating proteins from the cell, tissue, or body fluid sources from which a GP-83 protein is derived or substantially free from chemical precursors or thr chemcials when chemically synthesized. The term "substantially free of cellular material" includes preparations of GP-83 protein in which the protein is separated from cellular components of the cell from which it is isolated or recombinantly produced. Thus, GP-83 protein that is substantially free of cellular material includes preparations of GP-83 protein having less than about 30%, 20%, 10%, or 5% (by dry weight) of non-GP-83 protein (also referred to herein as a "contaminating protein"). When a GP-83 protein or biologically active portion thereof is recombinantly produced, it is also preferably substantially free of chemical precursors or other chemicals, i.e., it is separated from chemical precursors or other chemicals which are involved in the synthesis of the protein. Accordingly, such preparations of GP-83 protein have less than about 30%, 20%, 10%, or 5% (by dry weight) of chemical precursors or non-GP-83 chemicals.

Biologically active portions of a GP-83 protein include peptides comprising amino acid sequence sufficiently identical to or derived from the amino acid sequence of a GP-83 protein disclosed in SEQ ID NO: 2, which includes less amino acid than the full length GP-83 protein and exhibit at lease one activity of a GP-83 protein. A biologically active portion of a GP-83 protein can be a polypeptide which is, for example, 10, 25, 50, 100 or more amino acids in length. Other biologically active portions can be prepared by recombinant techniques and evaluated for one or more of the functional activities of a native GP-83 protein.

Preferred GP-83 protein has the amino acid sequence shown in SEQ ID NO: 2. Other useful GP-83 protein are substantially identical to SEQ ID NO: 2 and retain the biological activity of the protein of SEQ ID NO: 2. Difference in amino acid sequences may be due to natural allelic variation or mutagenesis. Accordingly, a useful GP-83 protein is a protein which includes an amino acid sequence at least about 50%, preferably 60%, 70%, 80%, 90%, 95%, 96%, 97%, 98% or 99% identical to the amino acid sequence of SEQ ID NO: 2 and retains the biological activity of GP-83 protein of SEQ ID NO: 2.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions× 100).

The determination of percent homology between two sequences can be accomplished using a mathematical algorithm. A preferred, non-limiting example of a mathematical algorithm utilized for the comparison of two sequences is the algorithm of Karlin and Altschul (1990) *Proc. Nat'l Acad. Sci. USA* 87:2264–2268, modified as in Karlin and Atlschul (1990) *J. Mol. Biol.* 215:403–410. BLAST nucleotide searches can be performed with the NBLAST program, score=100, wordlength=12 to obtain nucleotide sequences homologous to GP-83 nucleic acid molecule of the invention. BLAST protein searches can be performed with the XBLAST program, score=50, wordlength=3 to obtain nucleotide sequences analogous to GP-83 protein molecule of the invention. To obtain gapped alignments for comparison purposes, Gapped Blast can be utilized as described in Altschul et al., (1997) *Nucleic Acids Res.* 25:3389–3402. When utilized BLAST and Gapped BLAST programs, the default parameters of the respective programs can be used.

The invention also provides GP-83 chimeric or fusion proteins. The term "chimeric protein" or "fusion protein", as used herein, comprises a GP-83 polypeptide operatively linked to a non-GP-83 polypeptide. A "GP-83 polypeptide", as that term is used herein, refers to a polypeptide having an amino acid sequence corresponding to GP-83 protein, whereas "non-GP-83 polypeptide" refers to a polypeptide having an amino acid sequence corresponding to a protein which is not substantially identical to the GP-83 protein, i.e. a protein that is different from the GP-83 protein and is derived from the same or different organism. Within a GP-83 fusion protein, the GP-83 polypeptide can correspond to all or a portion of a GP-83 protein, preferably at least one biologically active portion of a GP-83 protein. Within the fusion protein, the term "operatively linked" is intended to indicate that the GP-83 polypeptide and the non-GP-83 polypeptide are fused in frame to each other. The non-GP-83 polypeptide can be fused to the N-terminus or C-terminus of the GP-83 polypeptide.

One useful fusion protein is a GST-GP-83 fusion protein in which the GP-83 sequences are fused to the C-terminus of the GST sequences. Such fusion proteins can facilitate the purification of recombinant GP-83.

In another embodiment, the fusion protein contains a signal sequence from another protein. In certain host cells (e.g. mammalian host cells), expression and/or secretion of GP-83 can be increased through the use of a heterologous signal sequence. For example, the gp67 secretory sequence of the baculovirus envelope protein can be used as a heterologous signal sequence (*Current Protocols in Molecular Biology*, Ausubel et al., eds., John Wiley & Sons, 1992).

Other example of eukaryotic heterologous signal sequences include the secretory sequences of melittin and human placental alkaline phosphatase (Stratagene; La Jolla, Calif.) In yet another example, useful prokaryotic heterologous signal sequences include the phoA secretory signal (*Molecular cloning*, Sambrook et al, second edition Cold Spring Harbor Laboratory Press, 1989) and the protein A secretory signal (Pharmacia Biotech; Piscataway, N.J.).

In yet another embodiment, the fusion protein is a GP-83-immunoglobulin fusion protein in which all or part of GP-83 is fused to sequences derived from a member of the immunoglobulin protein family. The GP-83 immunoglobulin fusion proteins of the invention can be incorporated into pharmaceutical compositions and administered to a subject to inhibit interaction between a GP-83 ligand and a GP-83 protein on the surface of a cell, to thereby suppress GP-83 mediated signal transduction in vivo. Moreover, the GP-83 immunoglobulin fusion proteins of the invention can be used as immunogens to produce anti-GP-83 antibodies in a subject, to purify GP-83 ligands and in screening assays to identify molecules which inhibit the interaction of GP-83 and GP-83 ligand.

Preferably, a GP-83 chimeric or fusion protein of the invention is produced b standard recombinant DNA techniques. For example, DNA fragments coding for the different polypeptide sequences are ligate together in-frame in accordance with conventional techniques, for example by employing blunt-ended or stagger-ended termini for ligation, restriction enzyme digestion to provide for appropriate termini, filling-in cohesive ends as appropriate, alkaline phosphatase treatment to avoid undesirable joining, and enzymatic ligation. In another embodiment, the fusion gene can by synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., *Current Protocols in Molecular Biology*, Ausubel et al. eds., John Wiley & Sons: 1992). Moreover, many expression vectors are commercially available that already encode a fusion moiety (E.g., a GST polypeptide). A GP-83-encoding nucleic acid can be cloned into such an expression vector such that the fusion moiety is linked in-frame to the GP-83 protein.

The present invention also pertains to variants of the GP-83 proteins which function as either GP-83 agonists or as GP-83 antagonists. Variants of the GP-83 protein can be generated by mutagenesis, e.g., discrete point mutation or truncation of the GP-83 protein. An antagonist of the GP-83 protein can inhibit one or more of the activities of the naturally occurring form of the GP-83 protein by, for example, competitively binding to a downstream or upstream member of a cellular signaling cascade which includes the GP-83 protein. Thus, specific biological effects an be elicited by treatment with a variant of limited function. Treatment of a subject with a variant having a subset of the biological activities of the naturally occurring form of the protein can have fewer side effects in a subject relative to treatment with the naturally occurring form of the GP-83 protein.

Also, an isolated GP-83 protein or a portion or fragment thereof, can be used as an immunogen to generate antibodies that bind GP-83 using standard techniques for polyclonal and monoclonal antibody preparation. The full-length GP-83 protein can be used or, alternatively, the invention provides antigenic peptide fragments of GP-83 for use as immunogens. The antigenic peptide of GP-83 comprises at least 8 (preferably 10, 15, 20, 30, 40, 50 or more) amino acid residues of amino acid sequence shown in SEQ ID NO: 2, and encompasses an epitope of GP-83 such that an antibody raised against the peptide forms a specific immune complex with GP-83.

A GP-83 immunogen typically is used to prepare antibodies by immunizing a suitable subject, (e.g., rabbit, goat, mouse or other mammal) with the immunogen. An appropriate immunogenic preparation can contain, for example, recombinantly expressed GP-83 protein or a chemically synthesized GP-83 polypeptide. The preparation can further include an adjuvant, such as Freund's complete or incomplete adjuvant, or similar immunostimulatory agent. Immunization of a suitable subject with an immunogenic GP-83 preparation induces a polyclonal anti-GP-83 antibody response.

Accordingly, another aspect of the invention pertains to anti-GP-83 antibodies. The term "antibody" as used herein refers to immunoglobulin molecules and immunologically active portions of immunoglobulin molecules, i.e., molecules that contain an antigen binding site which specifically binds an antigen, such as GP-83. A molecule which specifically binds GP-83 is a molecule which binds GP-83but does not substantially bind other molecules in a sample, e.g., a biological sample, which naturally contains GP-83. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind GP-83. The term "monoclonal antibody" or "monoclonal antibody composition" refers to a population of antibody molecules that contain only one species of an antigen binding site capable of immunoreacting with a particular epitope of GP-83. A monoclonal antibody composition thus typically displays a single binding affinity for a particular GP-83 protein with which it immunoreacts.

Polyclonal antibodies can be prepared as described above by immunizing a suitable subject with a GP-83 immunogen. The anti-GP-83 antibody titer in the immunized subject can be monitored over time by standard techniques, such as with an enzyme linked immunosorbent assay (ELISA) using immobilized GP-83. If desired, the antibody molecules directed against GP-83 can be isolated from the mammal (e.g., from the blood) and further purified by well-known techniques, such as protein A chromatography to obtain the IgG fraction. At an appropriate time after immunization, e.g., when the anti-GP-83 antibody titers are the highest, antibody-producing cells can be obtained from the subject and used to prepare monoclonal antibodies by standard techniques, such as the hyridoma technique originally described by Kohler and Milstein (1975) *Nature* 256: 495–497, the human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc. pp. 77–96) or trioma techniques. The technology for producing various antibodies' monoclonal antibody hybridoma is well known (see generally Current Protocols in Immunology (1994) Coligan et al. (eds.) John Wiley & Sons, Inc., New York, N.Y.). Briefly, an immortal cell line, typically a myeloma, is fused to lymphocytes, typically splenocytes, from a mammal immunized with a GP-83 immunogen as described above, and the culture supernatants of the resulting hybridoma cells are screened to identify a hybridoma producing a monoclonal antibody that binds GP-83.

Any of the many well known protocols used for fusing lymphocytes and immortalized cell lines can be applied for the purpose of generating an anti-GP-83 monoclonal antibody (see, e.g., Current Protocols in Immunology, supra; Galfre et al. (1977) Nature 266:55052; R. H. Kenneth, in *Monoclonal Antibodies: A new Dimension in biological Analyses*, Plenum Publishing Corp., New York, N.Y. (1980); and Lerner (1981) Yale J. Biol. Med. 54:387–402. Moreover, one of ordinary skill will appreciate that there are many variations of such method which also would be useful. Typically, the immortal cell line, such as a myeloma cell line, is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-AG4-1, P3-x63-Ag8.653 or Sp2/O-Ag14 myeloma lines. These myeloma lines are available from ATCC. Typically, HAT sensitive mouse myeloma cells are fused to mouse splenocytes using polyethylene glycol ("PEG"). Hybridoma resulting from the fusion are then selected using HAT medium, which kills unfused and unproductively fused myeloma cells (unfused splenocytes die after several days because they are not transformed). Hybridoma cells producing a monoclonal antibody of the invention are detected by screening hybridoma culture supernatants for antibodies that bind GP-83 using a standard ELISA assay.

Alternative to preparing monoclonal antibody-secreting hybridomas, a monoclonal anti-GP-83 antibody can be identified and isolated by screening recombinant combinatorial immunoglobulin library (e.g. an antibody phage display library) with GP-83 to thereby isolate immunoglobulin library member that bind GP-83. Kits for generating and screening phage display libraries are commercially available (e.g., the Pharmacia Recombinant Phage Antibody System Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication NO. WO 93/01288; PCT Publication No. WO 92/01047; PCT Publication No. WO 92/09690; PCT Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 26:1275–1281; Griffiths et al. (1993) *EMBO J* 12:725–734.

Additionally, recombinant anti-GP-83 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application; European Patent Application 173,494; PCT Publication No. WO 86/01533; U.S. Pat. No. 4,816,567; European Patent Application 125, 023; Better et al. (1988) *Science* 249:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314: 446–449; and Shaw et al. (1988) *J. Natl. Cancer Inst.* 80:1553–1559; Morrison (1985) *Science* 229:1202–1207; Oi et al. (1986) *Bio/Techniques* 4:214; U.S. Pat. No. 5,225, 539; Jones et al. (1986) *Nature* 321:552–525; Verhoeyan et al. (1988) *Science* 239:1534; and Beidler et al. (1988) *J. Immunol.* 141:4053–4060.

An anti-GP-83 antibody (e.g., monoclonal antibody) can be used to isolate GP-83 by standard techniques, such as affinity chromatography or immunoprecipitation. An anti-GP-83 antibody can facilitate the purification of natural GP-83 from cells and of recombinantly produced GP-83 expressed in host cells. Moreover, an anti-GP-83 antibody can be used to detect GP-83protein (e.g., in a cellular lysate or cell supernatant) in order to evaluate the abundance and pattern of expression of the GP-83 protein. Anti-GP-83 antibodies can be used diagnostically to monitor protein levels in tissue as part of a clinical testing procedure, e.g., to, for example, determine the efficacy of a given treatment regiment. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, flurorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin and examples of suitable radioactive material include $^{125}I$, $^{131}I$, $^{35}S$ or $^{3}H$.

III. Recombinant Expression Vectors and Host Cells

Another aspect of the invention relates to vectors, preferably expression vectors which contain a nucleic acid encoding GP-83 or a portion thereof. As used herein, the term "vector" refers to a nucleic acid molecule capable of transporting another nucleic acid to which it has been linked. One type of vector is a "plasmid", which refers to a circular double stranded DNA loop into which additional DNA sequence can be ligated. Another type of vector is a viral vector to which additional DNA segments can be ligated and added into the viral genome. Certain vectors are capable of autonomous replication in a host cell into which they are introduced (e.g., bacterial vectors having a bacterial original of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. In general, expression vectors of utility in recombinant DNA techniques are often in the form of plasmids. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadnylation signals). Such regulatory sequences are described for example, in Goeddel, *Gene Expression Technology: Methods in enzymology* 185, Academic Press, San Diego, Calif. (1990). Regulatory sequences include those which direct constitutive expression expression of a nucleotide sequence in many types of host cell and those which direct expression of the nucleotide sequence only in certain host cells such as a tissue specific regulatory sequences. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g. GP-83 proteins, mutant forms of GP-83, fusion proteins etc.). The recombinant expression vectors of the invention can be designed to express GP-83 in prokaryotic or eukaryotic cells, e.g., bacterial cells such as *E. coli* or insect cells (using baculovirus expression vectors), yeast cells, or mammalian cells. Suitable host cells are discussed further in Goeddel, *Gene Expression Technology: Methods in enzymology* 185, Academic Press, San Diego, Calif. (1990). Alternatively, the recombinant expression vector can be transcribed and translated in vitro, for example, using T7 promoter regulatory sequences and T7 polymerase.

Expression of proteins in prokaryotes is most often carried out in *E. Coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of recombinant protein; and 3) to aid in the purification of the recombinant protein by acting as a ligand in affinity purification. Often in fusion expression vectors, a proteolytic cleavage site is introduced a the junction of the fusion moiety and the recombinant protein to enable separation of the recombinant protein form the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc., Smith and Johnson (1988) *Gene* 67:31–40), pMAL (New England Biolabs, Beverly, Mass.) and pRIT5 (Pharmacia Piscataway, N.J.) which fuse glutathione S-transferase(GST), maltose E binding protein, or protein A respectively to the target recombinant protein.

Examples of suitable inducible non-fusion *E. coli* expression vectors include pTrc (Amann et al., (1988) *Gene* 69:301–315) and pET11d (Studier et al., *Gene Expression Technology: Methods in Enzymology* 185, Academic Press, San Diego Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS 174 (DE3) from a resident λ prophage harboring a T7 gn1 gene under the transcriptional control of the lacUV5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) Nucleic Acids Res. 20: 2111–2118). Such alteration of nucleic acid sequence of the invention can be carried out by standard DNA synthesis techniques.

In another embodiment, the GP-83 expression vector is a yeast expression vector. Examples of vectors for expression in yeast *S. cerivisae* include pYepSecl (Baldari et al. (1987) *EMBO J.* 6:229–234), pMFa (Kurjan and Herskowitz, (1982) *Cell* 30:933–943), pJRY88 (Schultz et al. (1987) *Gene* 54:113–123), pYES2 (Invitrogen Corporation, San Diego, Calif.), and picZ (Invitrogen Corporation, Sand Diego, Calif.).

Alternatively, GP-83 can be expressed in insect cells using baculovirus expression vectors. Baculovirus vectors available for expression of proteins in cultured insect cells (e.g., Sf 9 cells) include the pAc series (Smith et al (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapter 16 and 17 of Sambrook et al. (supra).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinker et al. (1987) *Genes Dev.* 1:268–277), lymphoic-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrno and Ruddle (1989) *Proc. Natl. Acad. Sci. USA* 86:5473–5477), pancrease-specific promoters (Edlund et al (1985) *Science* 230:912–916) and mammary gland-specific promoters (e.g., milk whey promoter; U.S. Pat. No. 264, 166). Developmentally-regulated promoters are also encompassed, for example the murine hox promoters (Kessel and Gruss (1990) *Science* 249:374–379) and the α-fetoprotein promoter (Campes and Tighman (1989) *Gene Dev.* 3:537–546).>epidyimis specific?

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to GP-83 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub et al. (*Reviews—Trends in Genetics*, Vol 1(1) 1986).

Another aspect of the invention relates to host cells into which a recombinant expression vector of the invention has been introduced. The term "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host call can be any prokaryotic or eukaryotic cell. For example, GP-83 protein can be expressed in bacterial cells such as *E. coli*, insect cells, yeast mammalian cells (such as Chinese hamster ovary cell (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art recognized techniques for introducing foreign nucleic acid (e.g., DNA) into a host cell, including calcium phosphate or calcium chloride co-precipitation, DEAE-dextran-mediate transfection, lipofection, or electroporaton. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding GP-83 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce, i.e. express, a GP-83 protein. Accordingly, the invention further provides methods for producing GP-83 protein using the host cells of the invention. In one embodiment, a host cell of the invention (into which a recombinant expression vector encoding GP-83 has been introduced) in a suitable medium such that GP-83 protein is produced. In another experiment, the method further comprises isolating GP-83 from the medium or the host cell.

The host cells of the invention can also be used to produced nonhuman transgenic animals. For example, in one embodiment, a host cell of the invention is a fertilized oocyte or an embryonic stem cell into which GP-83-encoding sequences have been introduced. Such host cells can then be used to create non-human transgenic animals in which exogenous GP-83 sequences have been introduced into their genome or homologous recombinant animals in which endogenous GP-83 sequences have been altered. Such animals are useful for studying the function and/or activity of GP-83 and for identifying and/or evaluating modulators of GP-83 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, or preferably a mouse, in which an endogenous GP-83 gene has been altered by homologous recombination between the endogenous gene and an exogenous DNA molecule introduced into cell of the animal, e.g., an embryonic cell of the animal, prior to development of the animal.

A transgenic animal of the invention can be created by introducing GP-83-encoding nucleic acid into the male pronuclei of a fertilized oocyte, e.g., by microinjection, retroviral infection, and allowing the oocyte to develop in a pseudopregnant female foster animal. The GP-83 cDNA sequence can be introduced as a transgene into the genome of a non-human animal. Alternatively, a nonhuman homologue of the human GP-83 gene can be isolated based on hybridization to the human GP-83 cDNA and used as a transgene. Intronic sequences and polyadenylation signals can also be included in the transgene to increase the efficiency of expression of the transgene. A tissue-specific regulatory sequences can be operably linked to the GP-83 transgene to direct expression of GP-83 protein to particular cells. Methods for generating transgenic animals via embryo manipulation and microinjection, particularly animals such as mice, have become conventional in the art and are described, for example, in U.S. Pat. Nos. 4,736,866, and 4,870,009, 4,873,191 and in Hogan, *Manipulating the Mouse Embryo*, (Cold Spring Harbor Laboratory Press, Colo. Spring Harbor, N.Y., 1986). Similar methods are used for production of other transgenic animals. A transgenic founder Animal can be identified based upon the presence of the GP-83 transgene in its genome and/or expression of GP-83 mRNA in tissues of cells of the animals. A transgenic founder animal can then be used to breed additional animals carrying the transgene. Moreover, transgenic animals carrying a transgene encoding GP-83 can further be bred to other transgenic animals carrying other transgenes.

To create a homologous recombinant animal, a vector is prepared which contains at least a portion of a GP-83 gene (e.g., a human or a non-human homolog of the GP-83 gene) into which a deletion, addition or substitution has been introduced to thereby alter, e.g. functionally disrupt, the GP-83 gene. In a preferred embodiment, the vector is designed such that upon homologous recombination, the endogenous GP-83 gene is functionally disrupted (i.e. no longer encodes a functional protein; also referred to as a "knock out" vector). Alternatively, the vector can be designed such that, upon homologous recombination, the endogenous GP-83 gene is mutated or otherwise altered but still encodes the functional protein (e.g. the upstream regulatory region can be altered to thereby alter the expression of the endogenous GP-83 protein). In the homologous recombination vector, the altered portion of the GP-83 gene is flanked at its 5' and 3' ends by additional nucleic acid of the GP-83 gene to allow for homologous recombination to occur between the exogenous GP-83 gene carried by the vector and an endogenous GP-83 gene in an embryonic stem cell. The additional flanking GP-83 nucleic acid is of sufficient length for successful homologous recombination with the endogenous gene. Typically, several kilo bases of flanking DNA (both at the 5' and 3' ends) and included in the vector (see, e.g., Thomas and Capecch (1987) *Cell* 51:503 for a description of homologous recombination vectors). The vector is introduced into an embryonic stem cell line (e.g., by electroporation) and cells in which the introduced GP-83 gene has homologously recombined with the endogenous GP-83 gene are selected (see, e.g., Li et al. (1992) *Cell* 69:915). The selected cells are then injected into a blastocyst of an animal (e.g., a mouse) to form aggregation chimera (see, e.g., Bradley in *Teratocarcinomas and Embryonic Stem Cells: A Practical Approach*, Robertson, ed. (IRL, Oxford (1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/losP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT Publication Nos. WO 97/07668 and WO 97/07669. In brief, a cell, e.g., a somatic cell, from the transgenic animal can be isolated and induced to exit the growth cycle and enter G. sub. o phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, i.e. the somatic cell, is isolated.

IV. Screening Assays

The nucleic acid molecules, proteins, protein homologues, and antibodies described herein can be used in screening assays.

The invention provides a method (also referred to herein as a "screening assay") for identifying modulators, i.e., candidate or test compounds or agents (e.g., peptides, peptidomimetics, small molecules or other drugs) which bind to GP-83 proteins or have a stimulatory or inhibitory effect on, for example, GP-83 expression or GP-83 activity.

In one embodiment, the invention provides assays for screening candidate or test compounds which bind to or modulate the activity of a GP-83 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des.* 12:145). Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223, 409), plasmids (Cull et al. (1992) *Proc. Natl. Acad. Sci. USA* 89:1865–1869) or on phage (Scott and Smith (1990) *Science* 249:386–390; Devlin (1990) *Science* 249:404–406; Cwirla et al. (1990) *Proc. Natl. Acad. Sci.* 87:6378–6382; and Felici (1991) *J. Mol. Biol.* 222:301–310).

Determining the ability of the test compound to modulate the activity of GP-83 or a biologically active portion thereof can be accomplished, for example, by determining the ability of the GP-83 protein to bind to or interact with a GP-83 target molecule. As used herein, a "target molecule" is a molecule with which a GP-83 protein binds or interacts in nature, for example, a molecule associated with the internal surface of a cell membrane or a cytoplasmic molecule. A GP-83 target molecule can be a non-GP-83 molecule or a GP-83 protein or polypeptide of the present invention. In one embodiment, a GP-83 target molecule is a component of a signal transduction pathway in spermatogenesis. The target, for example, can be a second intercellular protein which has catalytic activity or a protein which facilitates the association of downstream signaling molecules with GP-83.

Determining the ability of the GP-83 protein to bind to or interact with a GP-83 target molecule can be accomplished by one of the methods described above for determining direct binding. In a preferred embodiment, determining the ability of the GP-83 protein to bind to or interact with a GP-83 target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target an appropriate substrate, detecting the induction of a reporter gene (e.g., a GP-83-responsive regulatory element operatively linked to a nucleic acid encoding a detectable marker, e.g. luciferase), or detecting a cellular response, for example, cell survival, cellular differentiation, or cell proliferation.

In yet another embodiment, an assay of the present invention is a cell-free assay comprising contacting a GP-83 protein or biologically active portion thereof with a test compound and determining the ability of the test compound to bind to the GP-83 protein or biologically active portion thereof. Binding of the test compound to the GP-83 protein can be determined either directly or indirectly as described above. In a preferred embodiment, the assay includes contacting the GP-83 protein or biologically active portion thereof with a known compound which binds GP-83 to form an assay mixture, contacting the assay mixture with a test compound, and determining the ability of the test compound to interact with a GP-83 protein, wherein determining the ability of the test compound to interact with a GP-83 protein comprises determining the ability of the test compound to preferentially bind to GP-83 or biologically active portion thereof as compared to the known compound.

In another embodiment, an assay is a cell-free assay comprising contacting GP-83 protein or biologically active portion thereof with a test compound and determining the ability of the test compound to modulate (e.g., stimulate or inhibit) the activity of the GP-83 protein or biologically active portion thereof. Determining the ability of the test compound to modulate the activity of GP-83 can be accomplished, for example, by determining the ability of the GP-83 protein to bind to a GP-83 target molecule by one of the methods described above for determining direct binding. In an alternative embodiment, determining the ability of the test compound to modulate the activity of GP-83 can be accomplished by determining the ability of the GP-83 protein further modulate a GP-83 target molecule. For example, the catalytic/enzymatic activity of the target molecule on an appropriate substrate can be determined as previously described.

In yet another embodiment, the cell-free assay comprises contacting the GP-83 protein or biologically active portion thereof with a known compound which binds GP-83 to form an assay mixture, contacting the assay mixture with a test compound, and determining the ability of the test compound to interact with a GP-83 protein, wherein determining the ability of the test compound to interact with a GP-83 protein comprises determining the ability of the GP-83 protein to preferentially bind to or modulate the activity of a GP-83 target molecule. The cell-free assays of the present invention are amenable to use of both the soluble form or the membrane-associated form of GP-83. A membrane-associated form of GP-83 refers to GP-83 that interacts with a membrane-bound target molecule. In the case of cell-free assays comprising the membrane-associated form of GP-83, it may be desirable to utilize a solubilizing agent such that the membrane-associated form of GP-83 is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton.RTM. X-100, Triton-.RTM. X-114, Thesit.RTM., Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either GP-83 or its target molecule to facilitate separation of complexed from uncomplexed forms of one or both of the proteins, as well as to accommodate automation of the assay. Binding of a test compound to GP-83, or interaction of GP-83 with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/GP-83 fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or GP-83 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of GP-83 binding or activity determined using standard techniques.

Other techniques for immobilizing proteins on matrices can also be used in the screening assays of the invention. For example, either GP-83 or its target molecule can be immobilized utilizing conjugation of biotin and streptavidin. Biotinylated GP-83 or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with GP-83 or target molecules but which do not interfere with binding of the GP-83 protein to its target molecule can be derivatized to the wells of the plate, and unbound target or GP-83 trapped in the wells by antibody conjugation. Methods for detecting such complexes, in addition to those described above for the GST-immobilized complexes, include immunodetection of complexes using antibodies reactive with the GP-83 or target molecule, as well as enzyme-linked assays which rely on detecting an enzymatic activity associated with the GP-83 or target molecule.

In another embodiment, modulators of GP-83 expression are identified in a method in which a cell is contacted with a candidate compound and the expression of GP-83 mRNA or protein in the cell is determined. The level of expression of GP-83 mRNA or protein in the presence of the candidate compound is compared to the level of expression of GP-83 mRNA or protein in the absence of the candidate compound. The candidate compound can then be identified as a modulator of GP-83 expression based on this comparison. For example, when expression of GP-83 mRNA or protein is greater (statistically significantly greater) in the presence of the candidate compound than in its absence, the candidate compound is identified as a stimulator of GP-83 mRNA or protein expression. Alternatively, when expression of GP-83 mRNA or protein is less (statistically significantly less) in the presence of the candidate compound than in its absence, the candidate compound is identified as an inhibitor of GP-83 mRNA or protein expression. The level of GP-83 mRNA or protein expression in the cells can be determined by methods described herein for detecting GP-83 mRNA or protein.

In yet another aspect of the invention, the GP-83 proteins can be used as "bait proteins" in a two-hybrid assay or three hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Bio/Techniques 14:920–924; Iwabuchi et al. (1993) Oncogene 8:1693–1696; and PCT Publication No. WO 94/10300), to identify other proteins, which bind to or interact with GP-83 ("GP-83-binding proteins" or "GP-83-bp") and modulate GP-83 activity. Such GP-83-binding proteins are also likely to be involved in the propagation of signals by the GP-83 proteins as, for example, upstream or downstream elements of the GP-83 pathway.

The two-hybrid system is based on the modular nature of most transcription factors, which consist of separable DNA-binding and activation domains. Briefly, the assay utilizes two different DNA constructs. In one construct, the gene that codes for GP-83 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an GP-83-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with GP-83.

EXAMPLES

Example 1

Isolation and characterization of the h-ADAM7 cDNA encoding the GP-83 protein.

Construction of Epididymal cDNA Library

The cDNA expression library was constructed in □ ZAPII from human epididymis poly(A) RNA using a cDNA library synthesis kit (Stratagene, La Jolla, Calif., USA) according to the manufacturer's instructions. Briefly, total RNA was extracted from human corpus epididymis with Trizon (GibcoBRL, Rockville, Md., USA). The poly(A)$^+$ fraction was purified by oligo(dT)-cellulose column (Stratagene). Double-stranded cDNA was synthesized with 3–6 □g poly (A)$^+$ RNA template, ligated to EcoRI/XhoI digested □ ZAPII DNA, and subjected to in vitro packaging reaction.

The packaged library was plated on E. coli XL1-Blue MRF' and amplified as a plate lysate on agar plates (Sambrook et al., 1989). The titer of this library was $10^7$ plaque-forming units.

Immunoscreening and Cloning of GP-83 Expressing cDNA Clones

The cDNA clones encoding GP-83 were identified by immunoscreening as described by Huynh et al (1985) with modifications. The cDNA library was plated on E. coli XL1-blue cells and grown at 37° C. for 3–4 h. Recombinant protein expression was induced with 10 mM isopropyl-□-D-thiogalactopyranoside (IPTG)-saturated nitrocellulose (Schleicher and Schuell) at 37° C. for 4–5 h. Filters were removed, soaked in blocking solution (5% low fat milk powder, 0.05% Tween 20 in PBS) and washed in washing buffer (0.1% Tween 20 in PBS, PBST). Filters were reacted with GP-83 specific antiserum for 3 h at 4° C., then washed in PBST 3 times, and incubated with peroxidase-conjugated goat anti-rabbit IgG (1:3000 dilution, Sigma) at room temperature for 1 h. After washed, positive clones were revealed by a buffer containing 0.05M Tris-HCl, 0.1% $H_2O_2$ and 0.05% diaminobenzidine tetrahydrochloride (DAB), pH 7.6.

The positive clones were subjected to further subcloning. The inserts of the positive clones recovered from the $2^{nd}$ subcloning were amplified by T3 primer SEQ ID NO: 12 (5'-AATTA ACCCT CACTA AAGGG-3') and T7 primer SEQ ID NO: 13 (5'-GTAAT ACGAC TCACT ATAGG GC-3') in Taq polymerase system (Gibco BRL). The 5' end and 3' end sequences of the inserts were further cloned by rapid amplification of cDNA ends (RACE).

Cloning of the 5' and 3' end of Human ADAM7

The 5' end of GP-83 expressing cDNA recovered as described above was further cloned according to the protocols of "5' RACE System for rapid amplification of cDNA ends" (Gibco BRL). In brief, two primers, GPr160 SEQ ID NO: 14 (5'-TCGGT TCCTT AGTTT ATTGT G-3') and GPr50 SEQ ID NO: 15 (5'-TCCCT CATCT GAGTA TTTCA CTGGT TG-3') were designed from the 5' end of the 2.1 kb cDNA. GPr160 was annealed to human epididymis mRNA and cDNA was synthesized by SuperScript 11 reverse transcriptase (Gibco BRL). The mRNA template was degraded with RNase H. The single-stranded cDNA was purified with GlassMax Spin columns (Pharmacia, Piscataway, N.J., USA) and tailed on 3' end with homopolymer cytosine [ploy (C)] by terminal transferase. The tailed cDNA was amplified by PCR (Techne, FGENO2TP, Duxford, Cambridge, U. K.) with anchor primer SEQ ID NO: 16 (5'-CUACU ACUAC UAGGC CACGC GTCGA CTAGT ACGGG IIGGG IIGGG IIG 3') and GPr50 primer using the Taq polymerase system (Gibco BRL).

"Smart RACE cDNA Amplification Kit" (Clontech) was used for 3'-RACE. In brief, cDNA was amplified by reverse transcriptase using 3'-RACE cDNA synthesis primer SEQ ID NO: 17 (5-'AAGCA GTGGT AACAA CGCAG AGTAC $(T)_{30}N_{-1}N$-3'). The 3' ends of h-ADAM7 were further amplified by specific primer of h-ADAM7, Ls1718 SEQ ID NO: 18 (5'-AGATT TCTTC CCTGT GAGGA GA-3'), and SMART II oligonucleotide SEQ ID NO: 19 (5'-AAGCA GTGGT AACAA CGCAG AGTAC GCGGG-3') using the Taq polymerase system (Gibco BRL).

The products of 5'RACE and 3' RACE were purified by JET sorb Kit (Genomed), subcloned into pGEM-T vector (Promega) and transformed into competent *E. coli* XL-I Blue cells. Colonies were selected in the presence of ampicillin and sequenced as described below.

Sequence Analysis of cDNA Clones

The cDNA inserts were subjected to sequencing reaction with Rhodamine Terminator Cycle Sequencing Ready Reaction Kit (PE Applied Biosystems) on an ABI Prism 377 autosequencer according to the dideoxy chain-termination method (Sanger et al, 1977). The cDNA sequence encoding GP-83 and deduced amino acid sequence were analyzed by GenBank/EMBO databank using the GCG FASTA program (Pearson and Lipman, 1988).

Ex Vivo Expression of h-ADAM7

The h-ADAM7 cDNA (FIG. 1) was subcloned into a pRSET A vector (Invitrongen, San Diego, USA) at EcoRI restriction endonucleases sites to construct an expression plasmid. The resulting recombinant plasmid containing a 2.0-kb cDNA insert was designated as h-ADAM7p and transformed into competent *E. coli* BL21 (DE3) pLysS cells for protein expression. The h-ADAM7p-transformed cells were grown to a late log phase ($A_{600}$=0.4~0.5) in 2×YT broth, and induced to express proteins with 1 mM isopropyl-B-D-thiogalactoside (IPTG) for 2 h. The cells were recovered and sonicated in a buffer containing 8M urea, 0.1M $NaH_2PO_4$, 10 mM Tris-HCl, pH 8.0 to extract proteins.

Western Blot Analysis

The proteins expressed ex vivo were investigated for the presence of GP-83 by Western blotting using 5%/10% sodium dodecyl sulphate-polyacryamide gel eletrophoresis (Burnette, 1981). The blots were incubated with GP-83 antiserum or poly-His (Santa Cruz, Biotechnology, USA) antibody, followed by peroxidase-conjugated goat anti-rabbit IgG (Cappel, Turnhout, Belgium) and subsequently with enhanced luminol reagent (NEN, Boston, USA). Finally, the blots were exposed to X-ray film (X-Omat, Fuji, Japan) and the proteins that reacted with GP83 antiserum or poly-His antibody were revealed by chemiluminesce.

High Stringency Northern Blot Analysis

Northern blot analysis for tissue specificity was performed on Multiple Tissue Northern blots (Clontech, Palo Alto, Calif., USA) and total RNA recovered from the testis and epididymis of five patients with prostate carcinoma who received orchidectomy before hormone therapy at Tri-Service General Hospital, Taipei, Taiwan. Total RNA (5 □g) from testis, caput, corpus and cauda of epididymis were resolved on 1.2% formaldehyde-agarose gels and transferred onto Hybond-N filters (Sambrook et al., 1989). The filters were prehybridized at 45° C. for 1 h in a hybridization solution containing 50% deionized formamide, 5×SSC, 0.1% (w/v) N-lauroylsarcosine, 0.02% (w/v) SDS and 2% (w/v) blocking reagent (Boehringer Mannheim, Germany). The filters were then drained and replenished with fresh hybridization solution containing approximately 2.5 ng/ml probe, which was the 2.1-kb cDNA fragment labeled with digoxigenin using a random prime method (Boehringer Mannheim, Germany). The hybridization was allowed to proceed for 16–20 h at 45° C. Filters were washed in a buffer containing 0.1×SSC and 0.1% SDS at 68° C. for 20 min twice, then blocked in blocking reagent for 30 min. The filters were incubated with anti-digoxigenin-alkaline phosphatase solution (Boehringer Mannheim, Germany, 1:5,000 dilution) for 1 h, and subsequently with enhanced luminol reagent (NEN, Boston, USA). The filters were exposed to X-ray film (X-Omat, Fuji, Japan) and the transcripts reacted with the probe were revealed by chemiluminesce.

Example 2

Characterization of the GP-83 Protein

Figure 2:
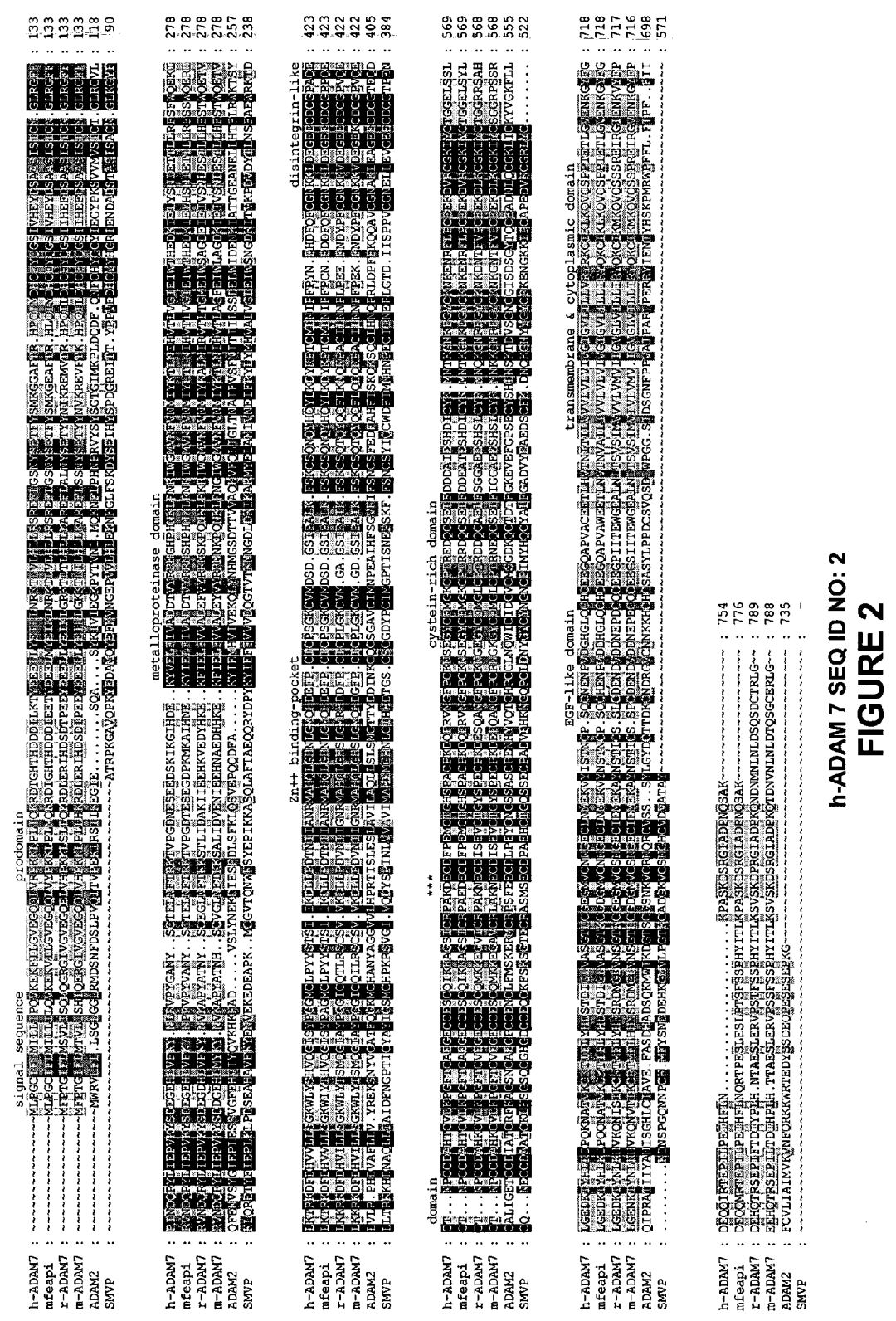

The identity of GP-83 encoding cDNA was determined by searching the GenBank and EMBL Data Banks, which revealed sequence homology to the metalloprotease and disintegrin domains of ADAM molecules (Wolfsberg et al., 1995 a, b). The cDNA sequence of GP-83 exhibited significant sequence homology to EAP-1 of the monkey and rat (Perry et al., 1992), and ADAM7 of mouse (Cornwall and Hsia, 1997) (FIG. 2). Therefore, these molecules are referred as ADAM7 of human, monkey, rat and mouse respectively (Wolfsberg and White, 1996; Stone et al, 1999).

Sequence analysis of GP-83, i.e. human ADAM7 (h-ADAM7) cDNA revealed a protein containing pro-domain (169 residues in all four species of ADAM7), metalloprotease domain (204 residues in human and monkey, 203 in mouse and rat), disintegrin domain (91 residues in all four species), cysteine-rich domain (141 residues), EGF-like domain (29 residues), transmembrane domain (64 residues in human, 68 residues in monkey, mouse and rat) and cytoplasmic domain (39 residues in human, 40 in monkey, 37 in mouse and rat) (FIG. 2).

Deduced amino acid sequence of GP-83 is 93.3%, 68.4% and 68% identical to those of ADAM7 proteins of the monkey, mouse and rat, respectively. There are seven potential N-linked glycosylation sites in h-ADAM7. The metalloproteinase domain of h-ADAM7 shares significant sequence similarity with those of monkey (95%), mouse (73%) and rat (70%) ADAM7. The metalloprotease domain of h-ADAM7 exhibits an active site sequence, <u>H</u>QLG <u>H</u>NLGMQ<u>H</u>D (SEQ ID NO: 20). According to Hite and his colleagues (1992), 3 histidine residues (H, underlined) bind zinc and the glycine residue (G, italicized) allows a turn. However, a glutamine (Q, bold) replaced the glutamate residue (E) in the catalytic site of h-ADAM7 as in those of the monkey, mouse and rat ADAM7 proteins (FIG. 2).

The disintegrin domain of h-ADAM7 shares 86% identity with that of monkey ADAM7, and 75% identity with those of mouse and rat. Although the binding motif of disintegrins in most of snake venom is RGD (Arg-Gly-Asp), putative integrin-binding sequence of h-ADAM7 is KDE as retrieved from homologous domains of other disintegrin, which also contains a negative charged residue at the carboxyl end of the tripeptides binding domain.

The intracellular domain of h-ADAM7 is the same as those of other species, which contains SH3 consensus sequences, RTEPILP (Alexandropoulos et al., 1995; Wolfsberg and White, 1996). Although the natural ligands for ADAM tails have not yet been identified, it is likely that some of these tails have signaling potential.

Example 3

Vector Construction

To obtain expression of GP-83 protein from the isolated h-ADAM7 cDNA, the h-ADAM7 cDNA was subcloned into the pRSET A vector. The proteins expressed in h-ADAM7-transformed competent *E. coli* BL21 (DE3) pLysS cells were examined on Western blots probed with GP-83 specific antiserum (Sun et al, 2000). Among newly expressed proteins that reacted with His-specific antibody, GP-83 was identified by specific antibody.

What is claimed is:

1. An isolated nucleic acid molecule comprising the nucleotide sequence of SEQ ID NO: 1 or a degenerate variant of SEQ ID NO: 1.

2. An expression vector comprising the nucleic acid molecule of claim 1 operably linked to an expression control sequence.

3. A cultured host cell comprising the vector of claim 2, or a progeny of said cell, wherein the cell expresses a polypeptide encoded by nucleotide sequence of SEQ ID NO: 1 or a degenerate variant of SEQ ID NO: 1.

4. A single stranded oligonucleotide consisting of the sequence of SEQ ID NO: 1 or a degenerate variant of SEQ ID NO: 1.

* * * * *

SEQUENCE LISTING

<160> NUMBER OF SEQ ID NOS: 6

<210> SEQ ID NO 1
<211> LENGTH: 3451
<212> TYPE: DNA
<213> ORGANISM: Homo sapiens
<220> FEATURE:
<221> NAME/KEY: exon
<222> LOCATION: (85)..(2409)

<400> SEQUENCE: 1

```
gatccctgca gtggaagtga ggaggaagaa aggtgaactc cttttctcaa gcacttctgc         60
tctcctctac cagaatcact caga atg ctt ccc ggg tgt ata ttc ttg atg          111
                           Met Leu Pro Gly Cys Ile Phe Leu Met
                            1               5 att tta ctc att cct cag gtt aaa gaa aag ttc atc ctt gga gta gag         159
Ile Leu Leu Ile Pro Gln Val Lys Glu Lys Phe Ile Leu Gly Val Glu
 10              15                  20                  25 ggt caa caa ctg gtt cgt cct aaa aag ctt cct ctg ata cag aag cga         207
Gly Gln Gln Leu Val Arg Pro Lys Lys Leu Pro Leu Ile Gln Lys Arg
             30                  35                  40 gat act gga cac acc cat gat gat gac ata ctg aaa acg tat gaa gaa         255
Asp Thr Gly His Thr His Asp Asp Asp Ile Leu Lys Thr Tyr Glu Glu
         45                  50                  55 gaa ttg ttg tat gaa ata aaa cta aat aga aaa acc tta gtc ctt cat         303
Glu Leu Leu Tyr Glu Ile Lys Leu Asn Arg Lys Thr Leu Val Leu His
     60                  65                  70 ctt cta aga tcc agg gag ttc cta ggc tca aat tac agt gaa aca ttc         351
Leu Leu Arg Ser Arg Glu Phe Leu Gly Ser Asn Tyr Ser Glu Thr Phe
 75                  80                  85 tac tcc atg aaa gga gga gcg ttc acc agg cat cct cag atc atg gat         399
Tyr Ser Met Lys Gly Gly Ala Phe Thr Arg His Pro Gln Ile Met Asp
 90                  95                 100                 105 cat tgt ttt tac caa gga tcc ata gta cac gaa tat gat tca gct gcc         447
His Cys Phe Tyr Gln Gly Ser Ile Val His Glu Tyr Asp Ser Ala Ala
                 110                 115                 120 agt atc agt acg tgt aat ggt cta agg gga ttc ttc aga ata aac gac         495
Ser Ile Ser Thr Cys Asn Gly Leu Arg Gly Phe Phe Arg Ile Asn Asp
             125                 130                 135 caa aga tac ctc att gaa cca gtg aaa tac tca gat gag gga gaa cat         543
Gln Arg Tyr Leu Ile Glu Pro Val Lys Tyr Ser Asp Glu Gly Glu His
         140                 145                 150 ttg gtg ttc aaa tat aac ctg agg gtg ccg tat ggt gcc aat tat tcc         591
Leu Val Phe Lys Tyr Asn Leu Arg Val Pro Tyr Gly Ala Asn Tyr Ser
     155                 160                 165 tgt aca gag ctt aat ttt acc aga aaa act gtt cca ggg gat aat gaa         639
Cys Thr Glu Leu Asn Phe Thr Arg Lys Thr Val Pro Gly Asp Asn Glu
170                 175                 180                 185 tct gaa gaa gac tcc aaa ata aaa ggc atc cat gat gaa aag tat gtt         687
Ser Glu Glu Asp Ser Lys Ile Lys Gly Ile His Asp Glu Lys Tyr Val
                 190                 195                 200 gaa ttg ttc att gtt gct gat gat act gtg tat cgc aga aat ggt cat         735
Glu Leu Phe Ile Val Ala Asp Asp Thr Val Tyr Arg Arg Asn Gly His
             205                 210                 215 cct cac aat aaa cta agg aac cga att tgg gga atg gtc aat ttt gtc         783
Pro His Asn Lys Leu Arg Asn Arg Ile Trp Gly Met Val Asn Phe Val
         220                 225                 230 aac atg att tat aaa acc tta aac atc cat gtg acg ttg gtt ggc att         831
Asn Met Ile Tyr Lys Thr Leu Asn Ile His Val Thr Leu Val Gly Ile
```

-continued

```
                235                 240                 245
gaa ata tgg aca cat gaa gat aaa ata gaa cta tat tca aat ata gaa    879
Glu Ile Trp Thr His Glu Asp Lys Ile Glu Leu Tyr Ser Asn Ile Glu
250                 255                 260                 265 act acc tta ttg cgt ttt tca ttt tgg caa gaa aag atc ctt aaa aca    927
Thr Thr Leu Leu Arg Phe Ser Phe Trp Gln Glu Lys Ile Leu Lys Thr
                270                 275                 280 cgg aag gat ttt gat cat gtt gta tta ctc agt ggg aag tgg ctc tac    975
Arg Lys Asp Phe Asp His Val Val Leu Leu Ser Gly Lys Trp Leu Tyr
            285                 290                 295 tca cat gtg caa gga att tct tat cca ggg ggt atg tgc ctg ccc tat   1023
Ser His Val Gln Gly Ile Ser Tyr Pro Gly Gly Met Cys Leu Pro Tyr
        300                 305                 310 tat tcc acc agt atc att aag gat ctt tta cct gac aca aac ata att   1071
Tyr Ser Thr Ser Ile Ile Lys Asp Leu Leu Pro Asp Thr Asn Ile Ile
    315                 320                 325 gca aac aga atg gca cat caa ctg ggg cat aac ctt ggg atg cag cat   1119
Ala Asn Arg Met Ala His Gln Leu Gly His Asn Leu Gly Met Gln His
330                 335                 340                 345 gac gag ttc cca tgc acc tgt cct tca gga aaa tgc gtg atg gac agt   1167
Asp Glu Phe Pro Cys Thr Cys Pro Ser Gly Lys Cys Val Met Asp Ser
                350                 355                 360 gat gga agc att cct gca ctg aaa ttc agt aaa tgc agc caa aac caa   1215
Asp Gly Ser Ile Pro Ala Leu Lys Phe Ser Lys Cys Ser Gln Asn Gln
            365                 370                 375 tac cac cag tac ttg aag gat tat aag cca aca tgc atg ctc aac att   1263
Tyr His Gln Tyr Leu Lys Asp Tyr Lys Pro Thr Cys Met Leu Asn Ile
        380                 385                 390 cca ttt cct tac aat ttt cat gat ttc caa ttt tgt gga aac aag aag   1311
Pro Phe Pro Tyr Asn Phe His Asp Phe Gln Phe Cys Gly Asn Lys Lys
    395                 400                 405 ttg gat gag ggt gaa gag tgt gac tgt ggc cct gct cag gag tgt act   1359
Leu Asp Glu Gly Glu Glu Cys Asp Cys Gly Pro Ala Gln Glu Cys Thr
410                 415                 420                 425 aat cct tgc tgt gat gca cac aca tgt gta ctg aag cca gga ttt act   1407
Asn Pro Cys Cys Asp Ala His Thr Cys Val Leu Lys Pro Gly Phe Thr
                430                 435                 440 tgt gca gaa gga gaa tgc tgt gaa tct tgt cag ata aaa aaa gca ggg   1455
Cys Ala Glu Gly Glu Cys Cys Glu Ser Cys Gln Ile Lys Lys Ala Gly
            445                 450                 455 tcc ata tgc aga ccg gcg aaa gat gaa tgt gat ttt cct gag atg tgc   1503
Ser Ile Cys Arg Pro Ala Lys Asp Glu Cys Asp Phe Pro Glu Met Cys
        460                 465                 470 act ggc cac tcg cct gcc tgt cct aag gac cag ttc agg gtc aat gga   1551
Thr Gly His Ser Pro Ala Cys Pro Lys Asp Gln Phe Arg Val Asn Gly
    475                 480                 485 ttt cct tgc aag aac tca gaa ggc tac tgt ttc atg ggg aaa tgt cca   1599
Phe Pro Cys Lys Asn Ser Glu Gly Tyr Cys Phe Met Gly Lys Cys Pro
490                 495                 500                 505 act cgt gag gat cag tgc tct gaa cta ttt gat gat gat gca ata gag   1647
Thr Arg Glu Asp Gln Cys Ser Glu Leu Phe Asp Asp Asp Ala Ile Glu
                510                 515                 520 agt cat gat atc tgc tac aag atg aat aca aaa gga aat aaa ttt gga   1695
Ser His Asp Ile Cys Tyr Lys Met Asn Thr Lys Gly Asn Lys Phe Gly
            525                 530                 535 tac tgc aaa aac aag gaa aac aga ttt ctt ccc tgt gag gag aaa gat   1743
Tyr Cys Lys Asn Lys Glu Asn Arg Phe Leu Pro Cys Glu Glu Lys Asp
        540                 545                 550 gtc aga tgt gga aag atc tac tgc act gga ggg gag ctt tcc tct ctc   1791
Val Arg Cys Gly Lys Ile Tyr Cys Thr Gly Gly Glu Leu Ser Ser Leu
```

```
                                                                    -continued Val Arg Cys Gly Lys Ile Tyr Cys Thr Gly Gly Glu Leu Ser Ser Leu
    555                 560                 565 ctt gga gaa gac aag act tat cac ctt aag gat ccc cag aag aat gct    1839
Leu Gly Glu Asp Lys Thr Tyr His Leu Lys Asp Pro Gln Lys Asn Ala
570                 575                 580                 585 act gtc aaa tgc aaa act att ttt tta tac cat gat tct aca gac att    1887
Thr Val Lys Cys Lys Thr Ile Phe Leu Tyr His Asp Ser Thr Asp Ile
                590                 595                 600 ggc ctg gtg gcg tca gga aca aaa tgt gga gag gga atg gtg tgc aac    1935
Gly Leu Val Ala Ser Gly Thr Lys Cys Gly Glu Gly Met Val Cys Asn
            605                 610                 615 aat ggt gaa tgt cta aac atg gaa aag gtc tat atc tca acc aat tgc    1983
Asn Gly Glu Cys Leu Asn Met Glu Lys Val Tyr Ile Ser Thr Asn Cys
        620                 625                 630 ccc tct cag tgc aat gaa aat cct gtg gat ggc cac gga ctc cag tgc    2031
Pro Ser Gln Cys Asn Glu Asn Pro Val Asp Gly His Gly Leu Gln Cys
    635                 640                 645 cac tgt gag gaa gga cag gca cct gta gcc tgt gaa gaa acc tta cat    2079
His Cys Glu Glu Gly Gln Ala Pro Val Ala Cys Glu Glu Thr Leu His
650                 655                 660                 665 gtt acc aat atc acc atc ttg gtt gtt gtg ctt gtc ctg gtt att gtc    2127
Val Thr Asn Ile Thr Ile Leu Val Val Val Leu Val Leu Val Ile Val
                670                 675                 680 ggt atc gga gtt ctt ata cta tta gtt cgt tac cga aaa tgt atc aag    2175
Gly Ile Gly Val Leu Ile Leu Leu Val Arg Tyr Arg Lys Cys Ile Lys
            685                 690                 695 ttg aag caa gtt cag agc cca cct aca gaa acc ctg gga gtg gag aac    2223
Leu Lys Gln Val Gln Ser Pro Pro Thr Glu Thr Leu Gly Val Glu Asn
        700                 705                 710 aaa gga tac ttt ggt gat gag cag cag ata agg act gag cca atc ctg    2271
Lys Gly Tyr Phe Gly Asp Glu Gln Gln Ile Arg Thr Glu Pro Ile Leu
    715                 720                 725 cca gaa att cat ttc cta aat aga act cca gaa tcc ttg gaa agc ctg    2319
Pro Glu Ile His Phe Leu Asn Arg Thr Pro Glu Ser Leu Glu Ser Leu
730                 735                 740                 745 ccc act agt ttt tca agt ccc cac tac atc aca ctg aaa cct gca agt    2367
Pro Thr Ser Phe Ser Ser Pro His Tyr Ile Thr Leu Lys Pro Ala Ser
                750                 755                 760 aaa gat tca aga gga atc gca gat ccc aat caa agt gcc aag           2409
Lys Asp Ser Arg Gly Ile Ala Asp Pro Asn Gln Ser Ala Lys
            765                 770                 775 tgagcttgaa gttggatatc caaaatggcc gtgcaagctt aggctgggga ttctggatgc  2469
aacgtcttta caaccttacc tagatatctg ctactcacat ttttggtagt gtttcaaacg  2529
ttctttatcc agacagacaa tgtttaagag aaacaactta tttctgttaa tatttaccgg  2589
tagaattcac accctctatc ataaacatat gctgcagaaa aaaatgtct tgtggtcttt    2649 caaatgctct ttagcacaat ataaaaattc gtaaccttgc tgtagtattt tcctacaaaa  2709
tgttactctg ctttctttta agaatccaaa ctttaaggat gataacttac agtctaagaa  2769
gaaaacattg catataaaaa gttactttttt tggaaacata aaagtacgtt ttaaaacttg  2829
aacatgacat cattagcact aattctggtt taaatgaaag tcctgcagaa atgccaaaga  2889
aggcagggca gagcggcacg gattctaggt aattaaaagt gaaagaggca gaagaatagt  2949
ggacagaact gcaggatagt ccttaaaata atggtggtgg gaaggaaaaa cacagaatgc  3009
tcctggcaat tctaaattcc taggtttgcc tttctagaat tccttaagaa gctgacagag  3069
aaatcagagg gttacaagaa tttcagaaaa tttactccaa gtgagaggac atactcacaa  3129
```

-continued

```
ctcctatgaa gggtttctaa ggtctttgtc ctgtgcaatt tgacaatgtg ccatttctgt    3189
gctgtctctg ccctctccct atccgtttgt tatgggatgg ggggttaccc tgggaatgat    3249
ttcagctgct tcttacacag atgcctctca aggtgttctt ttgtgtcctc tattttcttc    3309
ttgtgaactg ttaaagctac atgcattatt ttttttccat ttactgaaat aaagttttca    3369
agttctaaat aaaaatgttc tgactcgatg aaataaataa aggctacaaa agaaggaaga    3429
aaaaaaaaaa aaaaaaaaaa aa                                              3451
```

<210> SEQ ID NO 2
<211> LENGTH: 775
<212> TYPE: PRT
<213> ORGANISM: Homo sapiens
<220> FEATURE:
<221> NAME/KEY: LIPID
<222> LOCATION: (1)..(775)

<400> SEQUENCE: 2

```
Met Leu Pro Gly Cys Ile Phe Leu Met Ile Leu Leu Ile Pro Gln Val
1               5                   10                  15

Lys Glu Lys Phe Ile Leu Gly Val Glu Gly Gln Gln Leu Val Arg Pro
            20                  25                  30

Lys Lys Leu Pro Leu Ile Gln Lys Arg Asp Thr Gly His Thr His Asp
        35                  40                  45

Asp Asp Ile Leu Lys Thr Tyr Glu Glu Leu Leu Tyr Glu Ile Lys
    50                  55                  60

Leu Asn Arg Lys Thr Leu Val Leu His Leu Leu Arg Ser Arg Glu Phe
65                  70                  75                  80

Leu Gly Ser Asn Tyr Ser Glu Thr Phe Tyr Ser Met Lys Gly Gly Ala
                85                  90                  95

Phe Thr Arg His Pro Gln Ile Met Asp His Cys Phe Tyr Gln Gly Ser
            100                 105                 110

Ile Val His Glu Tyr Asp Ser Ala Ala Ser Ile Ser Thr Cys Asn Gly
        115                 120                 125

Leu Arg Gly Phe Phe Arg Ile Asn Asp Gln Arg Tyr Leu Ile Glu Pro
    130                 135                 140

Val Lys Tyr Ser Asp Glu Gly Glu His Leu Val Phe Lys Tyr Asn Leu
145                 150                 155                 160

Arg Val Pro Tyr Gly Ala Asn Tyr Ser Cys Thr Glu Leu Asn Phe Thr
                165                 170                 175

Arg Lys Thr Val Pro Gly Asp Asn Glu Ser Glu Asp Ser Lys Ile
            180                 185                 190

Lys Gly Ile His Asp Glu Lys Tyr Val Glu Leu Phe Ile Val Ala Asp
        195                 200                 205

Asp Thr Val Tyr Arg Arg Asn Gly His Pro His Asn Lys Leu Arg Asn
    210                 215                 220

Arg Ile Trp Gly Met Val Asn Phe Val Asn Met Ile Tyr Lys Thr Leu
225                 230                 235                 240

Asn Ile His Val Thr Leu Val Gly Ile Glu Ile Trp Thr His Glu Asp
                245                 250                 255

Lys Ile Glu Leu Tyr Ser Asn Ile Glu Thr Thr Leu Leu Arg Phe Ser
            260                 265                 270

Phe Trp Gln Glu Lys Ile Leu Lys Thr Arg Lys Asp Phe Asp His Val
        275                 280                 285

Val Leu Leu Ser Gly Lys Trp Leu Tyr Ser His Val Gln Gly Ile Ser
    290                 295                 300
```

```
Tyr Pro Gly Gly Met Cys Leu Pro Tyr Ser Thr Ser Ile Ile Lys
305                 310                 315                 320

Asp Leu Leu Pro Asp Thr Asn Ile Ile Ala Asn Arg Met Ala His Gln
            325                 330                 335

Leu Gly His Asn Leu Gly Met Gln His Asp Glu Phe Pro Cys Thr Cys
            340                 345                 350

Pro Ser Gly Lys Cys Val Met Asp Ser Asp Gly Ser Ile Pro Ala Leu
            355                 360                 365

Lys Phe Ser Lys Cys Ser Gln Asn Gln Tyr His Gln Tyr Leu Lys Asp
    370                 375                 380

Tyr Lys Pro Thr Cys Met Leu Asn Ile Pro Phe Pro Tyr Asn Phe His
385                 390                 395                 400

Asp Phe Gln Phe Cys Gly Asn Lys Lys Leu Asp Glu Gly Glu Glu Cys
                405                 410                 415

Asp Cys Gly Pro Ala Gln Glu Cys Thr Asn Pro Cys Cys Asp Ala His
            420                 425                 430

Thr Cys Val Leu Lys Pro Gly Phe Thr Cys Ala Glu Gly Glu Cys Cys
            435                 440                 445

Glu Ser Cys Gln Ile Lys Lys Ala Gly Ser Ile Cys Arg Pro Ala Lys
    450                 455                 460

Asp Glu Cys Asp Phe Pro Glu Met Cys Thr Gly His Ser Pro Ala Cys
465                 470                 475                 480

Pro Lys Asp Gln Phe Arg Val Asn Gly Phe Pro Cys Lys Asn Ser Glu
            485                 490                 495

Gly Tyr Cys Phe Met Gly Lys Cys Pro Thr Arg Glu Asp Gln Cys Ser
            500                 505                 510

Glu Leu Phe Asp Asp Asp Ala Ile Glu Ser His Asp Ile Cys Tyr Lys
    515                 520                 525

Met Asn Thr Lys Gly Asn Lys Phe Gly Tyr Cys Lys Asn Lys Glu Asn
530                 535                 540

Arg Phe Leu Pro Cys Glu Glu Lys Asp Val Arg Cys Gly Lys Ile Tyr
545                 550                 555                 560

Cys Thr Gly Gly Glu Leu Ser Ser Leu Leu Gly Asp Lys Thr Tyr
            565                 570                 575

His Leu Lys Asp Pro Gln Lys Asn Ala Thr Val Lys Cys Lys Thr Ile
            580                 585                 590

Phe Leu Tyr His Asp Ser Thr Asp Ile Gly Leu Val Ala Ser Gly Thr
    595                 600                 605

Lys Cys Gly Glu Gly Met Val Cys Asn Asn Gly Glu Cys Leu Asn Met
610                 615                 620

Glu Lys Val Tyr Ile Ser Thr Asn Cys Pro Ser Gln Cys Asn Glu Asn
625                 630                 635                 640

Pro Val Asp Gly His Gly Leu Gln Cys His Cys Glu Glu Gly Gln Ala
            645                 650                 655

Pro Val Ala Cys Glu Glu Thr Leu His Val Thr Asn Ile Thr Ile Leu
            660                 665                 670

Val Val Val Leu Val Leu Val Ile Gly Ile Gly Val Leu Ile Leu
            675                 680                 685

Leu Val Arg Tyr Arg Lys Cys Ile Lys Leu Lys Gln Val Gln Ser Pro
    690                 695                 700

Pro Thr Glu Thr Leu Gly Val Glu Asn Lys Gly Tyr Phe Gly Asp Glu
705                 710                 715                 720
```

-continued

```
Gln Gln Ile Arg Thr Glu Pro Ile Leu Pro Glu Ile His Phe Leu Asn
            725                 730                 735

Arg Thr Pro Glu Ser Leu Glu Ser Leu Pro Thr Ser Phe Ser Ser Pro
        740                 745                 750

His Tyr Ile Thr Leu Lys Pro Ala Ser Lys Asp Ser Arg Gly Ile Ala
            755                 760                 765

Asp Pro Asn Gln Ser Ala Lys
    770                 775

<210> SEQ ID NO 3
<211> LENGTH: 2634
<212> TYPE: DNA
<213> ORGANISM: Homo sapiens
<220> FEATURE:
<221> NAME/KEY: exon
<222> LOCATION: (85)..(2409)

<400> SEQUENCE: 3
gatccctgca gtggaagtga ggaggaagaa aggtgaactc cttttctcaa gcacttctgc        60
tctcctctac cagaatcact caga atg ctt ccc ggg tgt ata ttc ttg atg         111
                           Met Leu Pro Gly Cys Ile Phe Leu Met
                             1               5 att tta ctc att cct cag gtt aaa gaa aag ttc atc ctt gga gta gag        159
Ile Leu Leu Ile Pro Gln Val Lys Glu Lys Phe Ile Leu Gly Val Glu
 10              15                  20                  25 ggt caa caa ctg gtt cgt cct aaa aag ctt cct ctg ata cag aag cga        207
Gly Gln Gln Leu Val Arg Pro Lys Lys Leu Pro Leu Ile Gln Lys Arg
             30                  35                  40 gat act gga cac acc cat gat gat gac ata ctg aaa acg tat gaa gaa        255
Asp Thr Gly His Thr His Asp Asp Asp Ile Leu Lys Thr Tyr Glu Glu
         45                  50                  55 gaa ttg ttg tat gaa ata aaa cta aat aga aaa acc tta gtc ctt cat        303
Glu Leu Leu Tyr Glu Ile Lys Leu Asn Arg Lys Thr Leu Val Leu His
     60                  65                  70 ctt cta aga tcc agg gag ttc cta ggc tca aat tac agt gaa aca ttc        351
Leu Leu Arg Ser Arg Glu Phe Leu Gly Ser Asn Tyr Ser Glu Thr Phe
 75                  80                  85 tac tcc atg aaa gga gga gcg ttc acc agg cat cct cag atc atg gat        399
Tyr Ser Met Lys Gly Gly Ala Phe Thr Arg His Pro Gln Ile Met Asp
 90                  95                 100                 105 cat tgt ttt tac caa gga tcc ata gta cac gaa tat gat tca gct gcc        447
His Cys Phe Tyr Gln Gly Ser Ile Val His Glu Tyr Asp Ser Ala Ala
                 110                 115                 120 agt atc agt acg tgt aat ggt cta agg gga ttc ttc aga ata aac gac        495
Ser Ile Ser Thr Cys Asn Gly Leu Arg Gly Phe Phe Arg Ile Asn Asp
             125                 130                 135 caa aga tac ctc att gaa cca gtg aaa tac tca gat gag gga gaa cat        543
Gln Arg Tyr Leu Ile Glu Pro Val Lys Tyr Ser Asp Glu Gly Glu His
         140                 145                 150 ttg gtg ttc aaa tat aac ctg agg gtg ccg tat ggt gcc aat tat tcc        591
Leu Val Phe Lys Tyr Asn Leu Arg Val Pro Tyr Gly Ala Asn Tyr Ser
     155                 160                 165 tgt aca gag ctt aat ttt acc aga aaa act gtt cca ggg gat aat gaa        639
Cys Thr Glu Leu Asn Phe Thr Arg Lys Thr Val Pro Gly Asp Asn Glu
170                 175                 180                 185 tct gaa gaa gac tcc aaa ata aaa ggc atc cat gat gaa aag tat gtt        687
Ser Glu Glu Asp Ser Lys Ile Lys Gly Ile His Asp Glu Lys Tyr Val
                 190                 195                 200 gaa ttg ttc att gtt gct gat gat act gtg tat cgc aga aat ggt cat        735
Glu Leu Phe Ile Val Ala Asp Asp Thr Val Tyr Arg Arg Asn Gly His
```

-continued

|  | 205 | 210 | 215 |  |
|---|---|---|---|---|
| cct cac aat aaa cta agg aac cga att tgg gga atg gtc aat ttt gtc<br>Pro His Asn Lys Leu Arg Asn Arg Ile Trp Gly Met Val Asn Phe Val<br>220 225 230 | | | | 783 |
| aac atg att tat aaa acc tta aac atc cat gtg acg ttg gtt ggc att<br>Asn Met Ile Tyr Lys Thr Leu Asn Ile His Val Thr Leu Val Gly Ile<br>235 240 245 | | | | 831 |
| gaa ata tgg aca cat gaa gat aaa ata gaa cta tat tca aat ata gaa<br>Glu Ile Trp Thr His Glu Asp Lys Ile Glu Leu Tyr Ser Asn Ile Glu<br>250 255 260 265 | | | | 879 |
| act acc tta ttg cgt ttt tca ttt tgg caa gaa aag atc ctt aaa aca<br>Thr Thr Leu Leu Arg Phe Ser Phe Trp Gln Glu Lys Ile Leu Lys Thr<br>270 275 280 | | | | 927 |
| cgg aag gat ttt gat cat gtt gta tta ctc agt ggg aag tgg ctc tac<br>Arg Lys Asp Phe Asp His Val Val Leu Leu Ser Gly Lys Trp Leu Tyr<br>285 290 295 | | | | 975 |
| tca cat gtg caa gga att tct tat cca ggg ggt atg tgc ctg ccc tat<br>Ser His Val Gln Gly Ile Ser Tyr Pro Gly Gly Met Cys Leu Pro Tyr<br>300 305 310 | | | | 1023 |
| tat tcc acc agt atc att aag gat ctt tta cct gac aca aac ata att<br>Tyr Ser Thr Ser Ile Ile Lys Asp Leu Leu Pro Asp Thr Asn Ile Ile<br>315 320 325 | | | | 1071 |
| gca aac aga atg gca cat caa ctg ggg cat aac ctt ggg atg cag cat<br>Ala Asn Arg Met Ala His Gln Leu Gly His Asn Leu Gly Met Gln His<br>330 335 340 345 | | | | 1119 |
| gac gag ttc cca tgc acc tgt cct tca gga aaa tgc gtg atg gac agt<br>Asp Glu Phe Pro Cys Thr Cys Pro Ser Gly Lys Cys Val Met Asp Ser<br>350 355 360 | | | | 1167 |
| gat gga agc att cct gca ctg aaa ttc agt aaa tgc agc caa aac caa<br>Asp Gly Ser Ile Pro Ala Leu Lys Phe Ser Lys Cys Ser Gln Asn Gln<br>365 370 375 | | | | 1215 |
| tac cac cag tac ttg aag gat tat aag cca aca tgc atg ctc aac att<br>Tyr His Gln Tyr Leu Lys Asp Tyr Lys Pro Thr Cys Met Leu Asn Ile<br>380 385 390 | | | | 1263 |
| cca ttt cct tac aat ttt cat gat ttc caa ttt tgt gga aac aag aag<br>Pro Phe Pro Tyr Asn Phe His Asp Phe Gln Phe Cys Gly Asn Lys Lys<br>395 400 405 | | | | 1311 |
| ttg gat gag ggt gaa gag tgt gac tgt ggc cct gct cag gag tgt act<br>Leu Asp Glu Gly Glu Glu Cys Asp Cys Gly Pro Ala Gln Glu Cys Thr<br>410 415 420 425 | | | | 1359 |
| aat cct tgc tgt gat gca cac aca tgt gta ctg aag cca gga ttt act<br>Asn Pro Cys Cys Asp Ala His Thr Cys Val Leu Lys Pro Gly Phe Thr<br>430 435 440 | | | | 1407 |
| tgt gca gaa gga gaa tgc tgt gaa tct tgt cag ata aaa aaa gca ggg<br>Cys Ala Glu Gly Glu Cys Cys Glu Ser Cys Gln Ile Lys Lys Ala Gly<br>445 450 455 | | | | 1455 |
| tcc ata tgc aga ccg gcg aaa gat gaa tgt gat ttt cct gag atg tgc<br>Ser Ile Cys Arg Pro Ala Lys Asp Glu Cys Asp Phe Pro Glu Met Cys<br>460 465 470 | | | | 1503 |
| act ggc cac tcg cct gcc tgt cct aag gac cag ttc agg gtc aat gga<br>Thr Gly His Ser Pro Ala Cys Pro Lys Asp Gln Phe Arg Val Asn Gly<br>475 480 485 | | | | 1551 |
| ttt cct tgc aag aac tca gaa ggc tac tgt ttc atg ggg aaa tgt cca<br>Phe Pro Cys Lys Asn Ser Glu Gly Tyr Cys Phe Met Gly Lys Cys Pro<br>490 495 500 505 | | | | 1599 |
| act cgt gag gat cag tgc tct gaa cta ttt gat gat gat gca ata gag<br>Thr Arg Glu Asp Gln Cys Ser Glu Leu Phe Asp Asp Asp Ala Ile Glu<br>510 515 520 | | | | 1647 |
| agt cat gat atc tgc tac aag atg aat aca aaa gga aat aaa ttt gga<br> | | | | 1695 |

| | | |
|---|---|---|
| Ser His Asp Ile Cys Tyr Lys Met Asn Thr Lys Gly Asn Lys Phe Gly<br>525 530 535 | | |
| tac tgc aaa aac aag gaa aac aga ttt ctt ccc tgt gag gag aaa gat<br>Tyr Cys Lys Asn Lys Glu Asn Arg Phe Leu Pro Cys Glu Glu Lys Asp<br>540 545 550 | | 1743 |
| gtc aga tgt gga aag atc tac tgc act gga ggg gag ctt tcc tct ctc<br>Val Arg Cys Gly Lys Ile Tyr Cys Thr Gly Gly Glu Leu Ser Ser Leu<br>555 560 565 | | 1791 |
| ctt gga gaa gac aag act tat cac ctt aag gat ccc cag aag aat gct<br>Leu Gly Glu Asp Lys Thr Tyr His Leu Lys Asp Pro Gln Lys Asn Ala<br>570 575 580 585 | | 1839 |
| act gtc aaa tgc aaa act att ttt tta tac cat gat tct aca gac att<br>Thr Val Lys Cys Lys Thr Ile Phe Leu Tyr His Asp Ser Thr Asp Ile<br>590 595 600 | | 1887 |
| ggc ctg gtg gcg tca gga aca aaa tgt gga gag gga atg gtg tgc aac<br>Gly Leu Val Ala Ser Gly Thr Lys Cys Gly Glu Gly Met Val Cys Asn<br>605 610 615 | | 1935 |
| aat ggt gaa tgt cta aac atg gaa aag gtc tat atc tca acc aat tgc<br>Asn Gly Glu Cys Leu Asn Met Glu Lys Val Tyr Ile Ser Thr Asn Cys<br>620 625 630 | | 1983 |
| ccc tct cag tgc aat gaa aat cct gtg gat ggc cac gga ctc cag tgc<br>Pro Ser Gln Cys Asn Glu Asn Pro Val Asp Gly His Gly Leu Gln Cys<br>635 640 645 | | 2031 |
| cac tgt gag gaa gga cag gca cct gta gcc tgt gaa gaa acc tta cat<br>His Cys Glu Glu Gly Gln Ala Pro Val Ala Cys Glu Glu Thr Leu His<br>650 655 660 665 | | 2079 |
| gtt acc aat atc acc atc ttg gtt gtt gtg ctt gtc ctg gtt att gtc<br>Val Thr Asn Ile Thr Ile Leu Val Val Val Leu Val Leu Val Ile Val<br>670 675 680 | | 2127 |
| ggt atc gga gtt ctt ata cta tta gtt cgt tac cga aaa tgt atc aag<br>Gly Ile Gly Val Leu Ile Leu Leu Val Arg Tyr Arg Lys Cys Ile Lys<br>685 690 695 | | 2175 |
| ttg aag caa gtt cag agc cca cct aca gaa acc ctg gga gtg gag aac<br>Leu Lys Gln Val Gln Ser Pro Pro Thr Glu Thr Leu Gly Val Glu Asn<br>700 705 710 | | 2223 |
| aaa gga tac ttt ggt gat gag cag cag ata agg act gag cca atc ctg<br>Lys Gly Tyr Phe Gly Asp Glu Gln Gln Ile Arg Thr Glu Pro Ile Leu<br>715 720 725 | | 2271 |
| cca gaa att cat ttc cta aat aga act cca gaa tcc ttg gaa agc ctg<br>Pro Glu Ile His Phe Leu Asn Arg Thr Pro Glu Ser Leu Glu Ser Leu<br>730 735 740 745 | | 2319 |
| ccc act agt ttt tca agt ccc cac tac atc aca ctg aaa cct gca agt<br>Pro Thr Ser Phe Ser Ser Pro His Tyr Ile Thr Leu Lys Pro Ala Ser<br>750 755 760 | | 2367 |
| aaa gat tca aga gga atc gca gat ccc aat caa agt gcc aag<br>Lys Asp Ser Arg Gly Ile Ala Asp Pro Asn Gln Ser Ala Lys<br>765 770 775 | | 2409 |
| tgagcttgaa gttggatatc caaaatggcc gtgcaagctt aggctgggga ttctggatgc | | 2469 |
| aacgtctttα caaccttacc tagatatctg ctactcacat ttttggtagt gtttcaaacg | | 2529 |
| ttctttatcc agacagacaa tgtttaagag aaacaactta tttctgttaa tatttaccgg | | 2589 |
| tagaattcac accctctatc ataaacatat gctgcagaaa aaaaa | | 2634 |

<210> SEQ ID NO 4
<211> LENGTH: 681
<212> TYPE: DNA
<213> ORGANISM: Homo sapiens
<220> FEATURE:
<221> NAME/KEY: gene
<222> LOCATION: (1)..(681)

<400> SEQUENCE: 4

```
gagcttaatt ttaccagaaa aactgttcca ggggataatg aatctgaaga agactccaaa      60
ataaaaggca tccatgatga aaagtatgtt gaattgttca ttgttgctga tgatactgtg     120
tatcgcagaa atggtcatcc tcacaataaa ctaaggaacc gaatttgggg aatggtcaat     180
tttgtcaaca tgatttataa aaccttaaac atccatgtga cgttggttgg cattgaaata     240
tggacacatg aagataaaat agaactatat tcaaatatag aaactacctt attgcgtttt     300
tcattttggc aagaaaagat ccttaaaaca cggaaggatt ttgatcatgt tgtattactc     360
agtgggaagt ggctctactc acatgtgcaa ggaatttctt atccaggggg tatgtgcctg     420
ccctattatt ccaccagtat cattaaggat cttttacctg acacaaacat aattgcaaac     480
agaatggcac atcaactggg gcataacctt gggatgcagc atgacgagtt cccatgcacc     540
tgtccttcag gaaaatgcgt gatggacagt gatggaagca ttcctgcact gaaattcagt     600
aaatgcagcc aaaaccaata ccaccagtac ttgaaggatt ataagccaac atgcatgctc     660
aacattccat ttccttacaa t                                                681
```

<210> SEQ ID NO 5
<211> LENGTH: 276
<212> TYPE: DNA
<213> ORGANISM: Homo sapiens
<220> FEATURE:
<221> NAME/KEY: gene
<222> LOCATION: (1)..(276)

<400> SEQUENCE: 5

```
tttcatgatt tccaattttg tggaaacaag aagttggatg agggtgaaga gtgtgactgt      60
ggccctgctc aggagtgtac taatccttgc tgtgatgcac acacatgtgt actgaagcca     120
ggatttactt gtgcagaagg agaatgctgt gaatcttgtc agataaaaaa agcagggtcc     180
atatgcagac cggcgaaaga tgaatgtgat tttcctgaga tgtgcactgg ccactcgcct     240
gcctgtccta aggaccagtt cagggtcaat ggattt                                276
```

<210> SEQ ID NO 6
<211> LENGTH: 324
<212> TYPE: DNA
<213> ORGANISM: Homo sapiens
<220> FEATURE:
<221> NAME/KEY: gene
<222> LOCATION: (1)..(324)

<400> SEQUENCE: 6

```
aatatcacca tcttggttgt tgtgcttgtc ctggttattg tcggtatcgg agttcttata      60
ctattagttc gttaccgaaa atgtatcaag ttgaagcaag ttcagagccc acctacagaa     120
accctgggag tggagaacaa aggatacttt ggtgatgagc agcagataag gactgagcca     180
atcctgccag aaattcattt cctaaataga actccagaat ccttggaaag cctgcccact     240
agttttttcaa gtccccacta catcacactg aaacctgcaa gtaaagattc aagaggaatc     300
gcagatccca atcaaagtgc caag                                             324
```